(12) United States Patent
Fujisaki et al.

(10) Patent No.: US 9,962,247 B2
(45) Date of Patent: *May 8, 2018

(54) COLORED TRANSLUCENT ZIRCONIA SINTERED BODY AND POWDER, AND APPLICATION THEREOF

(71) Applicant: TOSOH CORPORATION, Yamaguchi (JP)

(72) Inventors: Hiroyuki Fujisaki, Yamaguchi (JP); Kiyotaka Kawamura, Yamaguchi (JP)

(73) Assignee: TOSOH CORPORATION, Yamaguchi (JP)

(*) Notice: Subject to any disclaimer, the term of this patent is extended or adjusted under 35 U.S.C. 154(b) by 0 days. days.

This patent is subject to a terminal disclaimer.

(21) Appl. No.: 15/321,011

(22) PCT Filed: Jun. 22, 2015

(86) PCT No.: PCT/JP2015/067845
§ 371 (c)(1),
(2) Date: Dec. 21, 2016

(87) PCT Pub. No.: WO2015/199018
PCT Pub. Date: Dec. 30, 2015

(65) Prior Publication Data
US 2017/0143458 A1  May 25, 2017

(30) Foreign Application Priority Data
Jun. 23, 2014 (JP) .................. 2014-128263

(51) Int. Cl.
*C04B 35/486* (2006.01)
*C04B 35/488* (2006.01)
(Continued)

(52) U.S. Cl.
CPC .......... *A61C 13/082* (2013.01); *A61C 13/083* (2013.01); *C04B 35/4885* (2013.01);
(Continued)

(58) Field of Classification Search
CPC .. C04B 35/486; C04B 35/4885; A61C 13/083
See application file for complete search history.

(56) References Cited

U.S. PATENT DOCUMENTS 4,742,030 A † 5/1988 Masaki
5,326,518 A * 7/1994 Kimura .................... B28B 1/24
264/328.2
(Continued)

FOREIGN PATENT DOCUMENTS

EP  0 218 853    4/1987
EP  2 263 988   12/2010
(Continued)

OTHER PUBLICATIONS

Umberto Anselmi-Tamburini et al., "Transparent Nanometric Cubic and Tetragonal Zirconia Obtained by High-Pressure Pulsed Electric Current Sintering"; Advanced Functional Materials 17; 2007; pp. 3267-3273.
(Continued)

*Primary Examiner* — Karl E Group
(74) *Attorney, Agent, or Firm* — Greenblum & Bernstein, P.L.C.

(57) ABSTRACT

A zirconia sintered body is provided having a color tone equivalent to the color tone guides of various natural teeth and having the same aesthetics as a natural front tooth. The present invention provides a colored translucent zirconia sintered body comprising zirconia containing greater than 4.0 mol % and not greater than 6.5 mol % of yttria, less than 0.25 mol % of erbia, less than 2,000 ppm of iron oxide in terms of $Fe_2O_3$, less than 0.01 wt. % of cobalt oxide in terms
(Continued)

of CoO, and less than 0.1 wt. % of alumina; the zirconia sintered body having a relative density of not less than 99.90%, a total light transmittance of not less than 25% and less than 40% for light having a wavelength of 600 nm at a sample thickness of 1.0 mm, and a strength of not less than 500 MPa.

11 Claims, 2 Drawing Sheets

(51) Int. Cl.
*A61C 13/083* (2006.01)
*A61C 13/08* (2006.01)
*C04B 35/64* (2006.01)

(52) U.S. Cl.
CPC ...... *C04B 35/64* (2013.01); *C04B 2235/3217* (2013.01); *C04B 2235/3224* (2013.01); *C04B 2235/3225* (2013.01); *C04B 2235/3246* (2013.01); *C04B 2235/3272* (2013.01); *C04B 2235/3275* (2013.01); *C04B 2235/5409* (2013.01); *C04B 2235/602* (2013.01); *C04B 2235/656* (2013.01); *C04B 2235/668* (2013.01); *C04B 2235/725* (2013.01); *C04B 2235/786* (2013.01); *C04B 2235/9653* (2013.01); *C04B 2235/9661* (2013.01)

(56) References Cited

U.S. PATENT DOCUMENTS

| | | | |
|---|---|---|---|
| 9,249,056 B2* | 2/2016 | Fujisaki | C04B 35/486 |
| 9,309,157 B2* | 4/2016 | Fujisaki | C04B 35/486 |
| 9,428,422 B2* | 8/2016 | Kawamura | A61K 6/0005 |
| 9,737,383 B2* | 8/2017 | Fujisaki | A61C 13/082 |
| 2009/0227438 A1 | 9/2009 | Fukatani et al. | |
| 2009/0246735 A1 | 10/2009 | Rogowski et al. | |
| 2010/0003630 A1† | 1/2010 | Yamashita | |
| 2011/0027742 A1* | 2/2011 | Fujisaki | C04B 35/486 433/8 |
| 2014/0227654 A1* | 8/2014 | Fujisaki | C04B 35/486 433/8 |
| 2016/0310245 A1* | 10/2016 | Fujisaki | C04B 35/486 |

FOREIGN PATENT DOCUMENTS

| | | |
|---|---|---|
| EP | 2 639 210 | 9/2013 |
| EP | 3 088 373 | 11/2016 |
| JP | 62-59571 | 3/1987 |
| JP | 62-153163 | 7/1987 |
| JP | 62153163 A † | 7/1987 |
| JP | 2005-289721 | 10/2005 |
| JP | 2008-50247 | 3/2008 |
| JP | 2008-222450 | 9/2008 |
| JP | 2009-207743 | 9/2009 |
| JP | 2010-501465 | 1/2010 |
| WO | 2008/013099 | 1/2008 |
| WO | 2009/125793 | 10/2009 |
| WO | 2013/018728 | 2/2013 |

OTHER PUBLICATIONS

International Search Report issued in Patent Application No. PCT/JP2015/067845, dated Sep. 8, 2015.
European Search Report issued in Patent Application No. 15812269.7, dated Dec. 1, 2017, along with an English translation of written opinion.

\* cited by examiner
† cited by third party

COLORED TRANSLUCENT ZIRCONIA SINTERED BODY AND POWDER, AND APPLICATION THEREOF

TECHNICAL FIELD

The present invention relates to a colored translucent zirconia sintered body having aesthetics very similar to those of a natural tooth and strength. The sintered body of the present invention can be used in dental applications, in particular, as a front tooth denture or a mill blank for a front tooth denture material.

BACKGROUND ART

Zirconia sintered bodies, in which yttria is solid-solved as a stabilizer, are used as dental materials such as dentures, by laminating porcelain or the like on the surface of the zirconia sintered body so as to adjust the color tone to be equivalent to that of a natural tooth. On the other hand, there is an increasing demand for zirconia sintered bodies which can be used directly as dental materials without laminating porcelain or the like. When a zirconia sintered body is used as a dental material, not only are mechanical properties of strength and toughness considered to be necessary, but optical characteristics such as translucency and color tone equivalent to those of a natural tooth are also required from an aesthetic standpoint.

For example, Patent Document 1 discloses a zirconia sintered body comprising from 2 to 4 mol % of yttria, wherein the alumina content is not greater than 0.2 wt. %, and the total light transmittance at a thickness of 1 mm is not less than 35%. A sintered body having a total light transmittance of 41% (total light transmittance of 36% for light having a wavelength of 600 nm at a thickness of 1.0 mm) disclosed in the working example has translucency and strength suitable for a back tooth denture. However, the color tone of this sintered body is white, so the sintered body cannot be used alone as a front tooth denture.

In addition, Patent Document 2 discloses a translucent zirconia sintered body which is colored yellow by adding Fe. This sintered body has a color tone closer to that of a natural tooth than a zirconia sintered body that does not contain Fe. However, this sintered body still has a color tone that differs from that of a natural tooth. Because the color tone difference between the sintered body and a natural tooth is substantial, as described above, the sintered body cannot be used alone as a denture.

Patent Document 3 discloses a zirconia sintered body containing from 1.5 to 5 mol % of yttria and having a porosity of not greater than 0.6%. However, this sintered body is a zirconia sintered body obtained by pressure sintering using hot isostatic pressing (also called "HIP" hereafter). In addition, Patent Document 4 discloses a zirconia sintered body containing yttria in an amount of greater than 4 mol % and not greater than 7 mol % and having a total light transmittance of not less than 40% for light having a wavelength of 600 nm at a thickness of 1 mm. This sintered body is also a zirconia sintered body obtained by pressure sintering. Furthermore, Non-Patent Document 1 discloses a transparent zirconia sintered body obtained by performing spark plasma sintering (called "SPS" hereafter) on a zirconia powder containing 3 mol % of yttria or 8 mol % of yttria.

These special sintering methods such as pressure sintering or SPS increase the production cost of the zirconia sintered bodies. Therefore, these zirconia sintered bodies can only be used in limited applications. Moreover, the transparency of the zirconia sintered body disclosed in Patent Document 4 or Non-Patent Document 1 is too high. Therefore, these sintered bodies give an unnatural impression as a front tooth denture.

In addition, the method ordinarily used to produce a denture from a translucent zirconia sintered body is to mold a zirconia powder, to calcine the zirconia powder at a temperature equal to or lower than the sintering temperature of zirconia, to process the resultant pre-sintered body into the shape of a denture, and to sinter the processed pre-sintered body at the sintering temperature of zirconia. Therefore, a zirconia powder with which a high-density zirconia sintered body that can be obtained by sintering under normal pressure for a short amount of time is desirable.

Conventionally, in order to achieve the same aesthetics as a natural tooth, porcelain or the like is laminated on the surface of a zirconia sintered body so as to adjust the color tone, and this is used as a dental material (for example, see Patent Document 5). This dental material is a composite material comprising zirconia and a glass material differing in strength from zirconia. The strength of such a composite material was not sufficient for a dental material.

Therefore, zirconia sintered bodies for dental materials which make it possible to enhance aesthetics while maintaining strength, without laminating porcelain or the like, are being researched.

For example, zirconia sintered bodies having the same translucency as a natural tooth have been reported (Patent Document 6). The sintered bodies disclosed in Patent Document 6 are used directly as a dental material. These zirconia sintered bodies have the same translucency as a natural tooth. On the other hand, these sintered bodies have a different color tone than a natural tooth—that is, the original bright white color tone of zirconia.

In addition, a colored zirconia sintered body for a dental material containing oxides as a colorant has been reported (for example, Patent Document 7). However, this sintered body is obtained by adding a rare earth oxide acting as a stabilizer to zirconia as a raw material for a base composition by means of powder mixing. Therefore, such a colored zirconia sintered body has very low strength.

CITATION LIST

Patent Literature

Patent Document 1: WO2009/125793
Patent Document 2: WO2013/018728
Patent Document 3: Japanese Unexamined Patent Application Publication No. S62-153163A
Patent Document 4: Japanese Unexamined Patent Application Publication No. 2008-222450A
Patent Document 5: Japanese Unexamined Patent Application Publication No. 2009-207743A
Patent Document 6: Japanese Unexamined Patent Application Publication No. 2008-50247A
Patent Document 7: Japanese Translation of PCT Application No. 2010-501465A

Non-Patent Literature

Non-Patent Document 1: Adv. Funct. Mater. 2007, 17, 3267-3273

SUMMARY OF INVENTION

Technical Problem

An object of the present invention is to eliminate the conventional drawbacks and to provide a zirconia sintered body suitable as a front tooth denture having aesthetics equivalent to those of a natural front tooth and strength. Another object of the present invention is to provide a zirconia sintered body having a color tone equivalent to the color tone guides of various natural teeth and having the same aesthetics as a natural front tooth. Another object of the present invention is to provide a zirconia powder with which such a zirconia sintered body can be produced by means of a simple process without requiring a special sintering method such as pressure sintering.

Solution to Problem

The present inventors researched zirconia sintered bodies used as front tooth dentures. As a result, the present inventors discovered that a zirconia sintered body containing a specific colorant has aesthetics and strength that make it usable as a practical front tooth denture, without additive laminating treatment such as coating, and the present inventors thereby completed the present invention.

The present inventors further discovered that in order to obtain a zirconia sintered body suitable for a front tooth denture by means of pressureless sintering, it is necessary to control the composition or physical properties of the zirconia powder and, in particular, to combine specific zirconia-containing powders, and the present inventors thereby completed the present invention.

That is, the gist of the present invention is as follows.

[1] A colored translucent zirconia sintered body containing zirconia containing greater than 4.0 mol % and not greater than 6.5 mol % of yttria, less than 0.25 mol % of erbia, less than 2,000 ppm of iron oxide in terms of $Fe_2O_3$, less than 0.01 wt. % of cobalt oxide in terms of CoO, and less than 0.1 wt. % of alumina; the zirconia sintered body having a relative density of not less than 99.90%, a total light transmittance of not less than 25% and less than 40% for light having a wavelength of 600 nm at a sample thickness of 1.0 mm, and a strength of not less than 500 MPa.

[2] The colored translucent zirconia sintered body according to [1], wherein an average crystalgrain size is from 0.3 to 5.0 μm.

[3] The colored translucent zirconia sintered body according to [1] or [2], wherein a luminosity L* in an L*a*b color system is not less than 43 and not greater than 60.

[4] The colored translucent zirconia sintered body according to any one of [1] to [3], wherein a monoclinic phase transformation depth after being immersed for 24 hours in hot water at 140° C. is not greater than 5 μm.

[5] The colored translucent zirconia sintered body according to any one of [1] to [4], wherein a monoclinic phase ratio after being immersed for 72 hours in hot water at 140° C. is not greater than 5%.

[6] The colored translucent zirconia sintered body according to any one of [1] to [5], wherein a crystal phase contains tetragonal and cubic phases.

[7] A production method for the colored translucent zirconia sintered compact according to any one of [1] to [6] including:
a molding step of obtaining a green body by molding a zirconia powder composition containing greater than 4.0 mol % and not greater than 6.5 mol % of yttria, less than 0.25 mol % of erbia, less than 0.1 wt. % of an aluminum compound in terms of $Al_2O_3$, less than 2,000 ppm of iron compound in terms of $Fe_2O_3$, and less than 0.01 wt. % of cobalt compound in terms of CoO; and a sintering step of sintering the green body under normal pressure at 1,400 to 1,600° C.

[8] The production method according to [7], wherein the zirconia powder composition contains at least two types selected from the group consisting of: a zirconia mixed powder containing greater than 0 wt. % and less than 0.09 wt. % of an aluminum compound, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 2,000 ppm and not greater than 3,000 ppm of an iron compound in terms of $Fe_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 0.03 wt. % and not greater than 0.05 wt. % of a cobalt compound in terms of CoO, the remainder being zirconia stabilized with greater than 4 mol % and not greater than 6.5 mol % of yttria; and a zirconia mixed powder containing greater than 0 wt. % and less than 0.09 wt. % of an aluminum compound in terms of $Al_2O_3$, the remainder being zirconia stabilized with greater than 2 mol % and not greater than 5 mol % of erbia.

[9] The production method according to [7] or [8], wherein the iron compound is at least one selected from the group consisting of iron oxide hydroxide and iron oxide.

[10] The production method according to any one of [7] to [9], wherein the aluminum compound is alumina.

[11] A zirconia powder composition containing greater than 4.0 mol % and not greater than 6.5 mol % of yttria, less than 0.25 mol % of erbia, less than 2,000 ppm of iron compound in terms of $Fe_2O_3$, less than 0.01 wt. % of cobalt compound in terms of CoO, and less than 0.1 wt. % of alumina; the zirconia powder composition having a BET specific surface area of from 7 to 13 $m^2/g$.

[12] The powder composition according to [11], wherein the powder composition contains at least two types selected from the group consisting of: a zirconia mixed powder containing greater than 0 wt. % and less than 0.09 wt. % of an aluminum compound in terms of $Al_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 2,000 ppm and not greater than 3,000 ppm of an iron compound in terms of $Fe_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 0.03 wt. % and not greater than 0.05 wt. % of a cobalt compound in terms of CoO, the remainder being zirconia stabilized with greater than 4 mol % and not greater than 6.5 mol % of yttria; and a zirconia mixed powder containing greater than 0 wt. % and less than 0.09 wt. % of an aluminum compound in terms of $Al_2O_3$, the remainder being zirconia stabilized with greater than 2 mol % and not greater than 5 mol % of erbia.

[13] The zirconia powder composition according to [11] or [12], wherein the zirconia powder composition is composed of spray-granulated powder granules.

[14] A dental material comprising the colored translucent zirconia sintered body according to any one of [1] to [6].

Advantageous Effects of Invention

The present invention can provide a zirconia sintered body suitable as a front tooth denture having translucency equivalent to those of a natural front tooth and strength. Furthermore, the present invention can provide a zirconia sintered body having a color tone equivalent to the color tone guides of various natural teeth. In addition, the present invention can provide a zirconia powder with which such a zirconia sintered body can be produced by means of a simple process without requiring a high-cost sintering method such as pressure sintering.

The colored translucent zirconia sintered body of the present invention is particularly suitable as front tooth dental materials such as a front tooth denture, a front tooth crown, a front tooth bridge and a mill blank for a front tooth denture. Furthermore, the colored translucent zirconia sintered body of the present invention is suitable as a dental material such as a denture material or an orthodontic bracket.

DESCRIPTION OF EMBODIMENTS

The "stabilizer concentration" in the present invention refers to a value expressing the ratio of stabilizer/($ZrO_2$+stabilizer) in terms of mol %. In the present invention, a stabilizer is an element having a function of stabilizing the crystal phase of zirconia. Examples of the stabilizers include yttrium (Y), erbium (Er), magnesium (Mg), and cerium (Ce). The above formula gives the ratio when the stabilizer is expressed in terms of oxide.

The "additive content" refers to a value expressing the ratio of additives/($ZrO_2$+stabilizer+additives) in terms of wt. %. In the present invention, an additive is an element other than zirconia and stabilizers. Examples of the additives include iron, cobalt, and aluminum, and the above formula gives the ratio when the additive is expressed in terms of oxide.

The "relative density" is the ratio of the measured density ($\rho$) to the theoretical density ($\rho_0$) and is a value determined by the following equation.

Relative density (%)=($\rho/\rho_0$)×100

In the above equation, the measured density ($\rho$) is a value measured by Archimedes' method.

Here, the theoretical density ($\rho_0$) of a sintered body comprising zirconia containing additives, wherein the remainder contains yttria, can be found by the following Equation (1).

$$\rho_0 = 100/[(A/\rho_A)+(100-A)/\rho_X] \quad (1)$$

In Equation (1), $\rho_0$ is the theoretical density (g/cm$^3$), A is the content (wt. %) of additives in terms of oxide, $\rho_A$ is the theoretical density (g/cm$^3$) of additives in terms of oxide, and $\rho_X$ is the theoretical density (g/cm$^3$) of a zirconia sintered body containing X mol % of yttria.

In Equation (1), $\rho_X$ represents a value which differs depending on the crystal phase of the zirconia sintered body. In this specification, a value calculated from the equation described in J. Am. Ceram. Soc., 69[4] 325-32 (1986) (also called the "reference document" hereafter) may be used as the theoretical density $\rho_X$.

According to the reference document, the theoretical density of zirconia containing 5.5 mol % of yttria is 6.0484 g/cm$^3$ in the case of a tetragonal phase and 6.0563 g/cm$^3$ in the case of a cubic phase.

In the present invention, a tetragonal phase and a cubic phase are each present in an amount of 50% in the zirconia sintered body containing 5.5 mol % of yttria. Therefore, the theoretical density $\rho_X$ is 6.0524 g/cm$^3$.

Note that representative values of the theoretical density $\rho_X$ of zirconia containing yttria in Equation (1) are as follows.

Yttria content of 3.0 mol %: $\rho_X$=6.095 g/cm$^3$
Yttria content of 3.5 mol %: $\rho_X$=6.086 g/cm$^3$
Yttria content of 4.0 mol %: $\rho_X$=6.080 g/cm$^3$
Yttria content of 4.1 mol %: $\rho_X$=6.080 g/cm$^3$
Yttria content of 4.5 mol %: $\rho_X$=6.072 g/cm$^3$
Yttria content of 5.0 mol %: $\rho_X$=6.062 g/cm$^3$
Yttria content of 5.5 mol %: $\rho_X$=6.052 g/cm$^3$
Yttria content of 6.0 mol %: $\rho_X$=6.043 g/cm$^3$
Yttria content of 6.5 mol %: $\rho_X$=6.033 g/cm$^3$
Yttria content of 7.4 mol %: $\rho_X$=6.019 g/cm$^3$ When the sintered body contains a plurality of additives, Equation (1) should be considered as the following equation to determine the theoretical density.

$$\rho_0 = 100/[\{(A1/\rho_{A1})+(A2/\rho_{A2})+ \ldots +(An/\rho_{An})\}+\{100-(A1+A2+\ldots+An)\}/\rho_X] \quad (1)'$$

In Equation (1)', A1, A2, and An are each of the additive contents (wt. %), $\rho_{A1}$, $\rho_{A2}$, and $\rho_{An}$ are each the theoretical densities (g/cm$^3$) of the additives A1, A2, and An in terms of oxide, and $\rho_X$ is the theoretical density (g/cm$^3$) of a zirconia sintered body containing X mol % of yttria.

In this specification, $\rho_A$ is the theoretical density of $Al_2O_3$ (3.99 g/cm$^3$) when the additive is aluminum; the theoretical density of $Fe_2O_3$ (5.24 g/cm$^3$) when the additive is iron; and the theoretical density of CoO (6.40 g/cm$^3$) when the additive is cobalt.

The "crystallite size" is a value determined using Equation (2) from the XRD peaks (also called "main XRD peaks" hereafter) of the tetragonal (111) plane and the cubic (111) plane in powder X-ray diffraction (called "XRD" hereafter) measurements.

$$\text{Crystallite size} = \kappa\lambda/\beta \cos\theta \quad (2)$$

In Equation (2), $\kappa$ is Scherrer' constant, ($\kappa$=1); $\lambda$ is the measured X-ray wavelength ($\lambda$=1.541862 Å when CuK$\alpha$-rays are used as a radiation source); $\beta$ is the half-width (°) of a main XRD peak; and $\theta$ is the Bragg angle of a main XRD peak.

Note that main XRD peaks are XRD peaks that appear in the vicinity of 2$\theta$=30.1 to 30.2° in XRD using CuK$\alpha$-rays as a radiation source. These peaks are XRD peaks overlapping with the tetragonal (111) plane and the cubic (111) plane. When calculating the crystallite size, the main XRD peaks are subjected to peak processing without separating the tetragonal and cubic crystal peaks. The Bragg angle ($\theta$) of the main XRD peaks after peak processing and the half-width ($\beta$) of the main XRD peaks after mechanical width correction should be determined.

The "average particle size" of the zirconia powder is the median diameter, which is the median value of the cumulative curve of the particle size distribution expressed on the basis of volume; that is, the diameter of spheres of the same volume of particles yielding a particle size corresponding to 50% of the cumulative curve. This average particle size is a value measured by a particle size distribution measurement device using a laser diffraction method.

The colored translucent zirconia sintered body of the present invention (also called the "sintered body of the present invention" hereafter) will be described hereinafter.

The present invention is a colored translucent zirconia sintered body comprising zirconia containing greater than 4.0 mol % and not greater than 6.5 mol % of yttria, less than 0.25 mol % of erbia, less than 2,000 ppm by weight of iron oxide in terms of $Fe_2O_3$, less than 0.01 wt. % of cobalt oxide in terms of CoO, and less than 0.1 wt. % of alumina; the zirconia sintered body having a relative density of not less than 99.90%, a total light transmittance of not less than 25% and less than 40% for light having a wavelength of 600 nm at a sample thickness of 1.0 mm (also simply called the "total light transmittance" hereafter), and a strength of not less than 500 MPa.

The sintered body of the present invention contains greater than 4.0 mol % and not greater than 6.5 mol % of yttria, less than 0.25 mol % of erbia, less than 2,000 ppm by weight of iron oxide in terms of $Fe_2O_3$, less than 0.01 wt. % of cobalt oxide in terms of CoO, and less than 0.1 wt. % of alumina.

Furthermore, the sintered body of the present invention is the zirconia sintered body of either of the following A) or B), and preferably has a relative density of not less than 99.90%, a total light transmittance of not less than 25% and less than 40%, and a strength of not less than 500 MPa.

A) A colored translucent zirconia sintered body containing at least either greater than 0 mol % and less than 0.25 mol % of erbia or greater than 0 wt. % and less than 0.01 wt. % of cobalt oxide in terms of CoO, greater than 4 mol % and not greater than 6.5 mol % of yttria, greater than 0 ppm by weight and less than 2,000 ppm by weight of iron oxide in terms of $Fe_2O_3$, and greater than 0 wt. % and less than 0.1 wt. % of aluminum in terms of $Al_2O_3$.

B) A colored translucent zirconia sintered body containing greater than 0 mol % and less than 0.25 mol % of erbia, greater than 0 wt. % and less than 0.01 wt. % of cobalt oxide in terms of CoO, greater than 4 mol % and not greater than 6.5 mol % of yttria, greater than 0 ppm by weight and less than 2,000 ppm by weight of iron oxide in terms of $Fe_2O_3$, and greater than 0 wt. % and less than 0.1 wt. % of aluminum in terms of $Al_2O_3$.

Yttria ($Y_2O_3$) functions as a stabilizer. When the yttria content is not greater than 4.0 mol %, the translucency becomes dramatically lower than that of a natural front tooth. In addition, when the yttria content is greater than 6.5 mol %, the sense of transparency becomes too high. Such a zirconia sintered body gives an unnatural impression as a front tooth denture. In addition, when the yttria content is greater than 6.5 mol %, the strength becomes too low, so the zirconia can no longer be used for a long period of time as a front tooth denture. A particularly preferable yttria content is not less than 4.6 mol % and not greater than 6 mol %, not less than 5 mol % and less than 6 mol %, or not less than 5.1 mol % and not greater than 5.6 mol %.

The sintered body of the present invention contains colorants. The sintered body of the present invention contains erbium (Er) as erbia ($Er_2O_3$), iron (Fe) as iron oxide ($Fe_2O_3$), and cobalt (Co) as cobalt oxide (CoO). These function as colorants.

In order to obtain a sintered body having a color tone similar to that of a natural tooth, the total content of the colorants is preferably not less than 0.2 wt. %, more preferably not less than 0.5 wt. %, and even more preferably not less than 0.55 wt. %. On the other hand, when the content of the colorants becomes large, the translucency of the sintered body tends to decrease. In order to achieve the color tone of a natural front tooth, the total content of the colorants is preferably not greater than 3 wt. % and more preferably not greater than 2.5 wt. %. The total content of the colorants is more preferably not less than 0.55 wt. % and not greater than 2.5 wt. %, and is even more preferably not less than 0.7 wt. % and not greater than 2.1 wt. %. A preferable total content of the colorants is not less than 0.7 wt. % and not greater than 2.1 wt. %, not less than 0.7 wt. % and not greater than 1.6 wt. %, not less than 0.5 wt. % and not greater than 1.6 wt. %, or not less than 1.0 wt. % and not greater than 1.6 wt. %.

The sintered body of the present invention contains erbia. Erbia functions as a stabilizer and a colorant. As a result of containing erbia (erbium oxide), the sintered body of the present invention assumes a red tinge. The content of erbia is preferably not less than 0 mol % (0 wt. %), more preferably greater than 0 mol %, and even more preferably not less than 0.03 mol % (0.087 wt. %). Furthermore, the content of erbia is preferably less than 0.25 mol % (0.73 wt. %), more preferably less than 0.23 mol % (0.67 wt. %), and even more preferably not greater than 0.21 mol % (0.61 wt. %). The erbia content of the sintered body of the present invention is preferably not less than 0 mol % and less than 0.25 mol %, more preferably not less than 0 mol % and not greater than 0.22 mol % (0.64 wt. %), and even more preferably greater than 0 mol % and not greater than 0.22 mol %.

A particularly preferable erbia content is, for example, not less than 0.05 mol % (0.15 wt. %) and not greater than 0.25 mol % in the case of a sintered body with a color tone of a front tooth with a strong reddish brown tinge, not less than 0.03 mol % and not greater than 0.19 mol % (0.55 wt. %) in the case of a sintered body with a color tone of a front tooth with a strong reddish yellow tinge, not less than 0 mol % and not greater than 0.1 mol % (0.29 wt. %) in the case of a sintered body with a color tone of a front tooth with a strong gray color, and greater than 0 mol % and not greater than 0.17 mol % (0.49 wt. %) in the case of a sintered body with a color tone of a front tooth with a strong reddish gray color.

The sintered body of the present invention contains iron oxide. Iron oxide functions as a colorant. As a result of containing iron oxide, the sintered body of the present invention has a color tone similar to that of a natural tooth. In addition, by forming a sintered body which also has the translucency described below in addition to the synergistic coloration of iron oxide and at least either of cobalt or erbium, the sintered body has aesthetics equivalent to those of a natural front tooth. The content of iron oxide in the sintered body of the present invention is greater than 0 ppm by weight in terms of $Fe_2O_3$. The content of iron oxide is less than 2,000 ppm by weight (0.2 wt. %) in terms of $Fe_2O_3$. When the content of $Fe_2O_3$ is less than 2,000 ppm by weight, not greater than 1,500 ppm by weight, or not greater than 1,450 ppm by weight, the color tone of the sintered body assumes a light yellow color, which tends to yield a color tone closer to that of a natural tooth. The sintered body of the present invention should contain iron oxide. When the content of iron oxide is not less than 50 ppm by weight (0.005 wt. %), not less than 500 ppm by weight, not less than 600 ppm by weight, not less than 700 ppm by weight, or greater than 800 ppm by weight in terms of $Fe_2O_3$, the sintered body of the present invention assumes a natural color tone that is similar to that of a front tooth with a relatively light color tone.

The content of iron oxide is more preferably not less than 500 ppm by weight and less than 2,000 ppm by weight, even more preferably not less than 500 ppm by weight and not greater than 1,450 ppm by weight, even more preferably not less than 700 ppm by weight and not greater than 1,450 ppm by weight, and even more preferably greater than 800 ppm by weight and not greater than 1,450 ppm by weight in terms of $Fe_2O_3$.

The sintered body of the present invention may contain cobalt oxide. When the sintered body contains cobalt oxide, the content thereof is preferably less than 0.01 wt. %, more preferably less than 0.008 wt. %, and even more preferably not greater than 0.006 wt. % in terms of CoO. As a result of containing cobalt oxide, the sintered body of the present invention is imparted with a black tinge. By combining the coloration of iron oxide and cobalt oxide, it is easy to achieve a color tone similar to that of a natural tooth. Depending on the content of other colorants, the sintered body of the present invention may achieve the color tone of a natural tooth without containing cobalt oxide. Therefore, the cobalt content should be not less than 0 wt. %. When the sintered body of the present invention contains cobalt oxide, the sintered body preferably contains cobalt oxide in an amount of greater than 0 wt. %, more preferably not less than 0.0003 wt. %, and even more preferably not less than 0.0004 wt. %. The content of cobalt oxide in the sintered body of the present invention is, for example, preferably not less than 0 wt. % and not greater than 0.006 wt. %, more preferably greater than 0 wt. % and not greater than 0.006 wt. %, even more preferably greater than 0 wt. % and not greater than 0.0055 wt. %, and even more preferably not less than 0 wt. % and not greater than 0.0055 wt. %.

The cobalt oxide content is, for example, not less than 0 wt. % and not greater than 0.003 wt. % in the case of a sintered body with a color tone of a tooth with a strong reddish brown tinge, not less than 0 wt. % and not greater than 0.001 wt. % in the case of a sintered body with a color tone of a tooth with a strong reddish yellow tinge, not less than 0.001 wt. % and not greater than 0.006 wt. % in the case of a sintered body with a color tone of a tooth with a strong gray color, and greater than 0 wt. % and not greater than 0.003 wt. % in the case of a sintered body with a color tone of a tooth with a strong reddish gray color.

Note that the cobalt oxide is preferably CoO. Cobalt trioxide ($Co_3O_4$) is known as an oxide of cobalt, but $Co_3O_4$ has a different color tone than CoO. Accordingly, the sintered body of the present invention preferably contains no $Co_3O_4$. It can be confirmed that the sintered body of the present invention contains essentially no $Co_3O_4$ from the fact that there is no peak corresponding to $Co_3O_4$ in a powder X-ray diffraction (also called "XRD" hereafter) pattern.

The sintered body of the present invention exhibits aesthetics equivalent to those of a natural front tooth even without containing colorants other than erbia, iron oxide, and cobalt oxide. Therefore, the colorants contained in the sintered body of the present invention are preferably only erbia, iron oxide, and cobalt oxide, and it is unnecessary to contain other colorants. However, when used in applications other than front tooth dentures such as dental materials other than front teeth, exterior members, or decorative members, the sintered body may contain elements which are solid-solved in zirconia as necessary in order to make minute adjustments to the color tone. Examples of the elements which are solid-solved in zirconia include any one or more types of elements from group 3a (group 3), group 5a (group 5), group 6a (group 6), group 7a (group 7), group 8 (groups 8 to 10), and group 3b (group 13) of the periodic table (the notation in parentheses is according to the International Union of Pure and Applied Chemistry (IUPAC)).

The sintered body of the present invention contains alumina. The alumina content of the sintered body of the present invention may be not less than 0 wt. % and is more preferably not less than 0.03 wt. %. As a result of containing alumina, the strength is further enhanced, and changes in color tone after hydrothermal treatment are suppressed.

Furthermore, the alumina content of the sintered body of the present invention is less than 0.1 wt. %, preferably less than 0.075 wt. %, and more preferably not greater than 0.055 wt. %. When the alumina content is not less than 0.1 wt. %, the translucency is diminished. Such a zirconia sintered body has unnatural aesthetics as a front tooth denture. As a result of containing at least either erbia or cobalt oxide and iron oxide and having an alumina content of not less than 0.045 wt. % and not greater than 0.055 wt. %, not only are changes in color tone after hydrothermal treatment suppressed, but the sintered body also has moderately high translucency, which yields a sintered body having aesthetics closer to those of a natural front tooth.

When each composition of yttria, erbia, iron oxide, cobalt oxide, and alumina in the sintered body of the present invention is within the ranges described above, the sintered body of the present invention assumes a color tone equivalent to the color tones of various natural teeth with a large amount of individual variation. For example, in the case of a sintered body having a color tone of a color tone guide of a natural tooth and having the aesthetics of a front tooth with a strong reddish brown tinge, the preferable composition of the sintered body of the present invention contains greater than 4 mol % and not greater than 6 mol % and preferably not less than 5.1 mol % and not greater than 5.5 mol % of yttria, not less than 0.05 mol % (0.15 wt. %) and not greater than 0.25 mol % of erbia, not less than 0 wt. % and not greater than 0.003 wt. % of cobalt oxide, not less than 400 ppm by weight and not greater than 1,500 ppm by weight of iron oxide, and not less than 0.02 wt. % and not greater than 0.07 wt. % of alumina, and the remainder is zirconia.

Similarly, in the case of a sintered body having the aesthetics of a front tooth with a strong reddish yellow tinge, the preferable composition of the sintered body of the present invention contains greater than 4 mol % and not greater than 6 mol % and preferably not less than 5.2 mol % and not greater than 5.5 mol % of yttria, not less than 0.03 mol % (0.087 wt. %) and not greater than 0.19 mol % (0.55 wt. %) of erbia, not less than 0 wt. % and not greater than 0.0008 wt. % of cobalt oxide, not less than 500 ppm by weight and not greater than 1,200 ppm by weight of iron oxide, and not less than 0.02 wt. % and not greater than 0.07 wt. % of alumina, and the remainder is zirconia.

Similarly, in the case of a sintered body having the aesthetics of a front tooth with a strong gray tinge, the preferable composition of the sintered body of the present invention contains greater than 4 mol % and not greater than 6 mol % and preferably not less than 5.3 mol % and not greater than 5.6 mol % of yttria, not less than 0 mol % (0 wt. %) and not greater than 0.1 mol % of erbia, not less than 0.0001 wt. % and not greater than 0.006 wt. % of cobalt oxide, not less than 400 ppm by weight and not greater than 1,500 ppm by weight of iron oxide, and not less than 0.02 wt. % and not greater than 0.07 wt. % of alumina, and the remainder is zirconia.

Similarly, in the case of a sintered body having the aesthetics of a front tooth with a strong reddish gray tinge, the preferable composition of the sintered body of the present invention contains greater than 4 mol % and not greater than 6 mol % and preferably not less than 5.2 mol % and not greater than 5.5 mol % of yttria, greater than 0 mol % (0 wt. %) and not greater than 0.17 mol % (0.49 wt. %) of erbia, greater than 0 wt. % and not greater than 0.003 wt. % of cobalt oxide, not less than 700 ppm by weight and not greater than 1,300 ppm by weight of iron oxide, and not less than 0.02 wt. % and not greater than 0.07 wt. % of alumina, and the remainder is zirconia.

The sintered body of the present invention satisfies the composition ranges above, and the relative density is not less than 99.90%, preferably not less than 99.92%, more preferably not less than 99.93%, and even more preferably not less than 99.95%. As a result, the sintered body of the present invention has moderate translucency in spite of containing colorants, and the total light transmittance is not less than 25% and less than 40%.

The measured density of a zirconia sintered body differs depending on the types and quantities of additives or stabilizers. The measured density of the sintered body of the present invention may be, for example, not less than 6.03 g/cm$^3$ and not greater than 6.08 g/cm$^3$, not less than 6.03 g/cm$^3$ and not greater than 6.07 g/cm$^3$, not less than 6.03 g/cm$^3$ and not greater than 6.06 g/cm$^3$, not less than 6.03 g/cm$^3$ and not greater than 6.05 g/cm$^3$, or not less than 6.04 g/cm$^3$ and not greater than 6.06 g/cm$^3$. The measured density is preferably not less than 6.05 g/cm$^3$ and not greater than 6.07 g/cm$^3$ and more preferably not less than 6.05 g/cm$^3$ and not greater than 6.06 g/cm$^3$.

The sintered body contains tetragonal and cubic phases in the crystal phase. As a result, it is easier to achieve aesthetics equivalent to those of a natural front tooth. The weight ratio of cubic phases to tetragonal phases in the crystal phases of the sintered body of the present invention is preferably not less than 70 wt. % and not greater than 130 wt. % and more preferably not less than 80 wt. % and not greater than 120 wt. %. In particular, it is preferable for the tetragonal phase content to be greater than the cubic phase content, and the above ratio is preferably not less than 80 wt. % and less than 100 wt. % and even more preferably not less than 80 wt. % and not greater than 90 wt. %. The crystal phases and the weight ratios of the tetragonal and cubic phases in the crystal phases of the sintered body of the present invention can be confirmed by XRD measurement. For example, XRD peaks corresponding to tetragonal and cubic phases are confirmed by performing Rietveld analysis on an XRD pattern of the present invention, and the crystal phase thereof can be thereby confirmed.

The average crystal grain size of the sintered body of the present invention is from 0.3 to 5.0 μm, preferably from 0.4 to 3.0 μm, more preferably from 0.4 to 1.0 μm, and even more preferably from 0.6 to 1.0 μm.

The sintered body of the present invention preferably contains crystal grains comprising not greater than 1 μm of tetragonal crystals and crystal grains comprising from 1 to 2 μm of cubic crystals. Furthermore, the crystalgrains of the sintered body of the present invention preferably include crystal grains having a particle size of from 1 to 3 μm (also called "large crystal grains" hereafter) and crystal grains having a particle size of not greater than 0.5 μm (also called "small particle particles" hereafter), and the ratio of the number of small crystal grains to the number of large crystal grains is preferably greater than 1.0 and not greater than 3.0 and more preferably not less than 1.2 and not greater than 2.0. As a result of being a sintered body containing colorants and having a microstructure containing crystal grains of different grain sizes and containing a large amount of small crystalgrains, it is possible to achieve moderate strength while having aesthetics equivalent to those of a natural front tooth.

Furthermore, the sintered body of the present invention preferably does not have abnormally grown crystal grains (also called "abnormally grown grains" hereafter). Abnormally grown grains are grains having a crystal grain size of not less than 5.0 μm. Abnormally grown grains are generally produced by stabilizer segregation and cause decreases in the strength of the sintered body. In this way, the sintered body of the present invention does not include grains in which stabilizers or colorants are segregated or abnormally grown grains produced by this segregation in spite of containing colorants.

The total light transmittance of the sintered body of the present invention is preferably not less than 25%, more preferably not less than 28%, and even more preferably not less than 31%. When the total light transmittance is not less than 25%, the sintered body has moderate translucency as a front tooth denture. On the other hand, the total light transmittance is preferably less than 40%, more preferably not greater than 36.5%, even more preferably not greater than 35%, and even more preferably not greater than 34.7%. When the total light transmittance is not less than 40%, the translucency becomes too high.

The total light transmittance for D65 light rays at a sample thickness of 1.0 mm of the sintered body of the present invention (also called the "D65 transmittance" hereafter) may be, for example, not less than 30% and not greater than 45%, not less than 32% and not greater than 45%, not less than 32% and less than 44%, or not less than 32% and less than 42%. As a result, it becomes easy to achieve aesthetics of the same degree as those of a natural front tooth. A particularly preferable D65 transmittance differs depending on the color tone of the sintered body of the present invention but may be, for example, a D65 transmittance of not less than 32% and not greater than 45% when the sintered body has a color tone of a front tooth with a strong reddish brown tinge, a D65 transmittance of not less than 37% and not greater than 45% when the sintered body has a color tone of a front tooth with a strong reddish yellow tinge, a D65 transmittance of not less than 30% and not greater than 43% when the sintered body has a color tone of a front tooth with a strong gray color, and a D65 transmittance of not less than 35% and not greater than 40% when the sintered body has a color tone of a front tooth with a strong reddish gray color.

The luminosity L* in an L*a*b color system (also simply called "luminosity L*" or "L*" hereafter) of the sintered body of the present invention is preferably not less than 43 and not greater than 60 and more preferably not less than 45 and not greater than 59.

As a result of having moderate translucency and having a luminosity L* within this range, the sintered body of the present invention has aesthetics equivalent to those of a natural front tooth. Note that in the sintered body of the present invention, the total light transmittance tends to become lower as the value of the luminosity L* becomes smaller.

The color phase a* in the L*a*b color system (also simply called "color phase a*" or "a*") in the sintered body of the present invention is preferably not less than −5 and not greater than 5, more preferably not less than −4 and not greater than 4, and even more preferably not less than −3 and not greater than 3.

Furthermore, it is preferable for the color phase a* to be within this range and for the color phase b* in the L*a*b color system (also simply called "color phase b*" or "b*") to be not less than 2 and not greater than 20, more preferably not less than 3 and not greater than 19, and even more preferably not less than 4 and not greater than 18.

The color tone of the sintered body of the present invention is defined by the luminosity L*, the color phase a*, and the color phase b*. Here, when the luminosity L* value becomes large, the color tone becomes bright. Conversely, when the L* value becomes small, the color tone becomes dark. Furthermore, the color tone of the sintered body of the present invention is a value measured by condensing light passing through the sintered body and light reflected by the sintered body. Therefore, when the thickness or translucency of the sintered body changes, the color tone thereof also changes. Accordingly, the color tone of the sintered body of the present invention yields aesthetics differing from the color tone determined by the luminosity L*, the color phase a*, and the color phase b* of a sintered body having a color tone of an opaque zirconia sintered body not having translucency or the color tone of a sintered body with lower translucency than the translucency of the present invention. In the present invention, the color tone should be L*a* and b* in an L*a*b* color system measured by a method according to JIS Z8729.

Furthermore, the sintered body of the present invention preferably has little variation in color tone before and after exposure to a water-containing environment. Front teeth have a substantial effect on the expression or impression of a person. Because the sintered body of the present invention has little variation in color tone before and after exposure to a water-containing environment, it becomes unnecessary to re-exchange a denture due to aesthetic variation when used as a front tooth denture. Furthermore, even when the sintered body of the present invention is used for a long period of time as a front tooth denture, there is no concern that the expression or impression of the patient may be suddenly changed. As a result, the mental and physical burden on the patient using the front tooth denture is reduced.

In the present invention, the color tone difference (ΔE) determined from the following equation may be used as an indicator of the amount of change in color tone before and after exposure to a water-containing environment.

$$\Delta E = (\Delta L^{*2} + \Delta a^{*2} + \Delta b^{*2})^{1/2}$$

In the above equation, ΔE is the color tone difference of the sintered body before and after being immersed in hot water at 140° C., and ΔL*, Δa*, and Δb* are respectively the differences in the luminosity L*, color phase a*, and color phase b* of the sintered body before and after being immersed in hot water at 140° C.

The value of ΔE of the sintered body of the present invention is preferably not greater than 2.0 and more preferably not greater than 1.0. When ΔE is not greater than 2.0, differences in aesthetics become imperceptible to the naked eye. Furthermore, when ΔE is not greater than 1.0, changes in aesthetics become difficult to perceive by the naked eye when the sintered body is compared before and after use. The sintered body of the present invention preferably has little variation in aesthetics when used over a longer period of time, and ΔE is preferably the value when immersed for 20 hours or longer in hot water at 140° C. and more preferably the value when immersed for 70 hours or longer in hot water at 140° C. For example, when the sintered body of the present invention is immersed for 24 hours in hot water at 140° C., ΔE may be not less than 0 and not greater than 0.5 or not less than 0.1 and not greater than 0.4. When the sintered body of the present invention is immersed for 72 hours in hot water at 140° C., ΔE may be not less than 0 and not greater than 1.0 or not less than 0.1 and not greater than 0.8.

The values of L*, a*, and b* of the sintered body of the present invention are preferably within the aforementioned ranges of L*, a*, and b*. When L*, a*, and b* are within the above ranges, the sintered body of the present invention has a color tone equivalent to the color tone guides (also called "shade guides") of various natural teeth. Examples of the shade guides include the shade guide "VITAPAN (trademark) classical" of the VITA Corporation (also called "VITA shade" hereafter) and the "Vintage Halo NCC Shade Guide" of the Shofu Inc. The aesthetics differ depending on the type of shade guide, but the sintered body of the present invention particularly preferably has a color tone equivalent to that of the VITA shade.

In this way, the sintered body of the present invention has moderate translucency in addition to the color tone of a natural tooth. Therefore, the sintered body of the present invention has aesthetics equivalent to those of a natural front tooth.

The strength of the sintered body of the present invention is preferably not less than 500 MPa, more preferably not less than 600 MPa, and even more preferably not less than 600 MPa and not greater than 1,200 MPa. When used as a front tooth denture and the difference in strength relative to a natural front tooth is too large, the enamel of the occluding natural tooth may be damaged. Therefore, the strength of the sintered body of the present invention is preferably not greater than 1,000 MPa, more preferably not less than 500 MPa and not greater than 850 MPa, even more preferably not less than 650 MPa and not greater than 850 MPa, even more preferably not less than 650 MPa, and not greater than 800 MPa, and even more preferably not less than 650 MPa and not greater than 750 MPa. Note that the strength in the present invention is the bending strength; in particular, the three-point bending strength, and more particularly the three-point bending strength measured in accordance with JIS R 1601.

When a zirconia sintered body is exposed to a water-containing environment, a monoclinic phase is produced in the crystal phase. When a monoclinic phase is produced, the aesthetics vary substantially. It is preferable that a monoclinic phase is unlikely to be produced in the sintered body of the present invention even when exposed to a water-containing environment. Therefore, the monoclinic phase ratio (also called the "M-phase ratio" hereafter) of the sintered body of the present invention after being immersed for 24 hours in hot water at 140° C. (also called "hydrothermal treatment") is preferably not greater than 10%, more preferably not greater than 5%, even more preferably not greater than 3%, and even more preferably not greater than 1%. The M-phase ratio is an indicator of the degradation of the zirconia sintered body in a water-containing environment. When the M-phase ratio is within this range, the sintered body can be used for a longer period of time as a front tooth denture.

Here, the M-phase ratio is a value calculated from the following equation after taking XRD measurements for the mirror surface portion of the sintered body to determine the diffraction intensity of each of the (111) and (11-1) planes of the monoclinic phase, the (111) plane of the tetragonal phase, and the (111) plane of the cubic phase.

$$f_m = \{I_m(111) + I_m(11-1)\} / \{I_m(111) + I_m(11-1) + I_t(111) + I_c(111)\} \times 100$$

In the above equation, fm is the monoclinic phase ratio (%); $I_m(111)$ is the XRD peak intensity of the monoclinic phase (111) plane; $I_m(11-1)$ is the XRD peak intensity of the monoclinic phase (11-1) plane; $I_t(111)$ is the XRD peak intensity of the tetragonal phase (111) plane; and $I_c(111)$ is the XRD peak intensity of the cubic phase (111) plane.

Furthermore, the hydrothermal degradation of the sintered body accelerates as the hydrothermal treatment time becomes longer. Therefore, the M-phase ratio of the sintered body of the present invention after being immersed for 72 hours in hot water at 140° C. is not greater than 15%, preferably not greater than 10%, more preferably not greater than 5%, even more preferably less than 2%, and even more preferably not greater than 1%. As a result, the aesthetics of the sintered body of the present invention become unlikely to change even when used for a long period of time in an intraoral environment.

Note that although it is preferable for the M-phase ratio to be low, in reality there does not exist a zirconia sintered body in which a monoclinic phase is not produced in a hydrothermal environment. Therefore, the M-phase ratio of the sintered body of the present invention is greater than 0%.

The monoclinic phase transformation depth of the sintered body of the present invention after being immersed for 24 hours in hot water at 140° C. (also simply called the "transformation depth") is preferably not greater than 5 μm and more preferably not greater than 3 μm. The transformation depth can be used as an indicator of the degradation of a zirconia sintered body in a hydrothermal environment. That is, when the transformation depth is small, this serves as an indicator that the sintered body is unlikely to degrade even when used for a long period of time as a dental material. The transformation depth can be determined by observing a cross section of the sintered body by a scanning electron microscopy (SEM) or the like.

The transformation depth of the sintered body of the present invention after being immersed for 72 hours in hot water at 140° C. is preferably not greater than 10 μm and more preferably not greater than 5 μm.

Next, the production method of the sintered body of the present invention will be described.

The sintered body of the present invention can be obtained by a production method comprising: a molding step of obtaining a green body by molding a zirconia powder composition containing greater than 4.0 mol % and not greater than 6.5 mol % of yttria, less than 0.25 mol % of erbia, less than 0.1 wt. % of an aluminum compound in terms of $Al_2O_3$, less than 2,000 ppm by weight of iron compound in terms of $Fe_2O_3$, and less than 0.01 wt. % of cobalt compound in terms of CoO; and a sintering step of sintering the green body under normal pressure at 1,400 to 1,600° C.

More preferably, the sintered body of the present invention can be obtained by a production method comprising: a molding step of obtaining a green body by molding a zirconia powder composition containing at least either greater than 0 mol % and less than 0.25 mol % of erbia or greater than 0 wt. % and less than 0.01 wt. % of cobalt compound in terms of CoO, greater than 4 mol % and not greater than 6.5 mol % of yttria, greater than 0 ppm by weight and less than 2,000 ppm by weight of iron compound in terms of $Fe_2O_3$, and greater than 0 wt. % and less than 0.1 wt. % of aluminum compound in terms of $Al_2O_3$; and a sintering step of sintering the green body under normal pressure at a temperature of not lower than 1,400° C. and not higher than 1,600° C.

The zirconia powder composition used in the molding step (also simply called the "powder composition" hereafter) is a zirconia powder composition containing greater than 4.0 mol % and not greater than 6.5 mol % of yttria, less than 0.25 mol % of erbia, less than 2,000 ppm by weight of an iron compound in terms of $Fe_2O_3$, less than 0.01 wt. % of cobalt oxide in terms of CoO, and less than 0.1 wt. % of an aluminum compound in terms of $Al_2O_3$.

The following are examples of preferable powder compositions.

A) A zirconia powder composition containing at least either greater than 0 mol % and less than 0.25 mol % of erbia or greater than 0 wt. % and less than 0.01 wt. % of a cobalt compound in terms of CoO, greater than 4 mol % and not greater than 6.5 mol % of yttria, greater than 0 ppm by weight and less than 2,000 ppm by weight of an iron compound in terms of $Fe_2O_3$, and greater than 0 wt. % and less than 0.1 wt. % of an aluminum compound in terms of $Al_2O_3$.

B) A zirconia powder composition containing greater than 0 mol % and less than 0.25 mol % of erbia, greater than 0 wt. % and less than 0.01 wt. % of a cobalt compound in terms of CoO, greater than 4 mol % and not greater than 6.5 mol % of yttria, greater than 0 ppm by weight and less than 2,000 ppm by weight of an iron compound in terms of $Fe_2O_3$, and greater than 0 wt. % and less than 0.1 wt. % of an aluminum compound in terms of $Al_2O_3$.

The following are examples of particularly preferable powder compositions.

C) A powder composition containing at least two types selected from the group consisting of: a zirconia mixed powder containing greater than 0 wt. % and less than 0.09 wt. % of an aluminum compound in terms of $Al_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 2,000 ppm and not greater than 3,000 ppm of an iron compound in terms of $Fe_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 0.03 wt. % and not greater than 0.05 wt. % of a cobalt compound in terms of CoO, the remainder being zirconia stabilized with greater than 4 mol % and not greater than 6.5 mol % of yttria; and a zirconia mixed powder containing greater than 0 wt. % and less than 0.09 wt. % of an aluminum compound in terms of $Al_2O_3$, the remainder being zirconia stabilized with greater than 2 mol % and not greater than 5 mol % of erbia. This powder composition is preferably a zirconia powder composition containing at least either greater than 0 mol % and less than 0.25 mol % of erbia or greater than 0 wt. % and less than 0.01 wt. % of cobalt in terms of CoO, greater than 4 mol % and not greater than 6.5 mol % of yttria, greater than 0 ppm by weight and less than 2,000 ppm by weight of iron in terms of $Fe_2O_3$, and greater than 0 wt. % and less than 0.1 wt. % of aluminum in terms of $Al_2O_3$, the remainder being zirconia.

The powder composition contains a zirconia powder. The zirconia powder is preferably a stabilized zirconia powder and is more preferably a zirconia powder that is stabilized with at least either yttria or erbia. The zirconia powder is particularly preferably a zirconia powder that is stabilized with at least either less than 0.25 mol % of erbia or greater than 4 mol % and not greater than 6.5 mol % of yttria.

Because the density of the resulting sintered body becomes high, the crystallite size of the zirconia powder in the powder composition is preferably from 340 to 420 Å and more preferably from 350 to 410 Å.

Here, a preferable production method of the zirconia powder contained in the powder composition will be described.

The zirconia powder contained in the powder composition can be obtained, for example, by a production method comprising: a hydrolysis step of obtaining a hydrated zirconia sol by the hydrolysis of an aqueous solution of a zirconium salt; a drying step of obtaining a dry powder by drying the obtained hydrated zirconia sol; and a calcination step of obtaining a calcined powder by calcining the dry powder.

In the hydrolysis step, a hydrated zirconia sol is obtained by hydrolyzing a zirconium salt. The zirconium salt in the hydrolysis step may be a water-soluble zirconium compound. Examples of preferable zirconium salts include at least one type selected from the group consisting of zirconium oxychloride, zirconium nitrate, zirconium chloride, and zirconium sulfate, and mixtures of zirconium hydroxide and acids. The zirconium salt is preferably zirconium oxychloride.

In the drying step, the obtained hydrated zirconia sol is dried. When a zirconia powder that is stabilized with at least either erbia or yttria is used, it is preferable to mix at least either an yttrium compound or an erbium compound into the hydrated zirconia sol and to dry the mixture.

The yttrium compound mixed into the hydrated zirconia sol may be one that is soluble in acid and forms yttria after sintering. The yttrium compound may be at least one type selected from the group consisting of yttrium chloride, yttrium nitrate, and yttrium oxide, and the yttrium compound is more preferably at least either yttrium chloride or yttrium oxide.

The yttrium compound is preferably mixed into the hydrated zirconia sol so that the $Y_2O_3$ content with respect to zirconia ($ZrO_2$) in the hydrated zirconia sol is greater than 4 mol % and not greater than 6.5 mol %, preferably not less than 4.6 mol % and not greater than 6 mol %, more preferably not less than 5 mol % and less than 6 mol %, and even more preferably not less than 5.1 mol % and not greater than 5.5 mol %.

The erbium compound mixed into the hydrated zirconia sol may be one that is soluble in an acid and forms erbia after sintering. The erbium compound may be at least one type selected from the group consisting of erbium chloride, erbium nitrate, and erbium oxide, and the erbium compound is more preferably at least either erbium chloride or erbium oxide.

The erbium compound content with respect to zirconia ($ZrO_2$) in the hydrated zirconia sol is preferably not less than 0 mol %, more preferably greater than 0 mol %, and even more preferably not less than 0.03 mol % in terms of $E_2O_3$. Furthermore, the erbium compound is preferably less than 0.25 mol %, more preferably less than 0.23 mol %, and even more preferably not greater than 0.21 mol % in terms of $E_2O_3$. The erbium compound is preferably mixed into the hydrated zirconia sol so that the $Er_2O_3$ content is not less than 0 mol % and less than 0.25 mol %, more preferably not less than 0 mol % and not greater than 0.22 mol %, and even more preferably greater than 0 mol % and not greater than 0.22 mol %.

In the calcination step, the dry powder of the hydrated zirconia sol obtained in the drying step is calcined to obtain a calcined powder. As a result, a zirconia powder is obtained. From the perspectives of the cohesiveness and the particle size of the obtained zirconia powder, the calcination temperature is preferably from 1,050 to 1,250° C., more preferably from 1,100 to 1,200° C., and even more preferably from 1,100 to 1,180° C. A particularly preferable calcination temperature is higher than 1,150° C. and not higher than 1,180° C. or not lower than 1,155° C. and not higher than 1,180° C.

The obtained zirconia powder may be pulverized as necessary and is preferably pulverized after being formed into a zirconia mixed powder by mixing a zirconia powder and at least one type selected from the group consisting of aluminum compounds, iron compounds, and cobalt compounds (also called "added compounds" hereafter). By simultaneously mixing the added compounds and the zirconia powder, these components are mixed uniformly. In particular, when a water-insoluble compound is used as an added compound, it is preferable to mix the added compound and the zirconia powder and to then pulverize the mixture.

At least either an yttrium compound or an erbium compound (also called a "stabilizer raw material" hereafter) may be mixed at the time of the pulverization of the zirconia powder. However, the stabilizer raw material that is mixed at the time of pulverization easily segregates in the sintered body in the sintering step. Therefore, the stabilizer raw material is preferably mixed into a hydrated zirconia sol, dried, and calcined so as to form a solid solution with zirconia and preferably not mixed at the time of pulverization.

From the perspectives of the pulverization time, formability, and sintering performance, pulverization is preferably performed so that the average particle size is from 0.40 to 0.50 μm and more preferably from 0.40 to 0.45 μm.

The powder composition contains an iron compound and an aluminum compound and may contain a cobalt compound as necessary. Below, the contents of the iron compound, cobalt compound, and aluminum compound are each values determined in terms of $Fe_2O_3$, CoO, and $Al_2O_3$.

The powder composition contains less than 2,000 ppm of an iron compound in terms of $Fe_2O_3$. The iron compound should contain iron and form iron oxide after sintering. The iron compound may be at least one type selected from the group consisting of iron chloride, iron nitrate, iron oxide, and iron oxide hydroxide, and at least either iron oxide or iron oxide hydroxide may be preferably used.

The iron compound is preferably mixed so that the content thereof is less than 2,000 ppm (0.2 wt. %), more preferably not greater than 1,800 ppm (0.18 wt. %), even more preferably not greater than 1,600 ppm by weight (0.16 wt. %), even more preferably not greater than 1,500 ppm by weight, and even more preferably not greater than 1,000 ppm by weight. The powder composition should contain an iron compound, and the content of the iron compound should be greater than 0 ppm by weight. The content of the iron compound may be not less than 50 ppm by weight (0.005 wt. %), not less than 500 ppm by weight, not less than 600 ppm by weight, not less than 700 ppm by weight, or greater than 800 ppm by weight.

The content of the iron compound is more preferably not less than 500 ppm by weight and less than 2,000 ppm by weight, even more preferably not less than 500 ppm by weight and not greater than 1,450 ppm by weight, even more preferably not less than 700 ppm by weight and not greater than 1,450 ppm by weight, and even more preferably greater than 800 ppm by weight and not greater than 1,450 ppm by weight.

The powder composition contains less than 0.01 wt. %, preferably less than 0.008 wt. %, and more preferably not greater than 0.006 wt. % of a cobalt compound in terms of CoO. The cobalt content should be not less than 0 wt. %, and when the sintered body of the present invention contains a cobalt compound, the content thereof is preferably greater than 0 wt. % and more preferably not less than 0.0003 wt. %. The content of the cobalt compound is, for example, preferably not less than 0 wt. % and not greater than 0.006 wt. %, more preferably greater than 0 wt. % and not greater than 0.006 wt. %, even more preferably greater than 0 wt. % and not greater than 0.0055 wt. %, and even more preferably not less than 0 wt. % and not greater than 0.0055 wt. %.

The cobalt compound should contain cobalt and form cobalt oxide after sintering. The cobalt compound may be at least one type selected from the group consisting of cobalt chloride, cobalt nitrate, and cobalt oxide, and is preferably cobalt oxide. The cobalt compound is preferably less than 0.01 wt. % of cobalt oxide, more preferably greater than 0 wt. % and not greater than 0.01 wt. % of cobalt oxide, and even more preferably greater than 0 wt. % and not greater than 0.006 wt. % of cobalt oxide.

The powder composition contains less than 0.1 wt. % and preferably not greater than 0.07 wt. % of an aluminum compound in terms of $Al_2O_3$. The aluminum compound should contain aluminum and form alumina after sintering. The aluminum compound may be at least one type selected from the group consisting of alumina, hydrated alumina, alumina sol, aluminum hydroxide, aluminum chloride, aluminum nitrate, and aluminum sulfate, preferably at least one type selected from the group consisting of alumina, hydrated alumina, and alumina sol, more preferably alumina, and even more preferably α-alumina. The powder composition contains less than 0.1 wt. %, preferably not greater than 0.07 wt. %, and more preferably not greater than 0.055 wt. % of an aluminum compound. A more preferable aluminum compound content is not less than 0.045 wt. % and not greater than 0.055 wt. %.

The powder mixture is obtained by mixing an yttria compound, a zirconia powder, an iron compound, an aluminum compound, and, if necessary, at least either a cobalt compound or an erbium compound. For example, a powder composition may be prepared by mixing a zirconia powder with an erbium compound, an yttrium compound, an aluminum compound, a cobalt compound, and an iron compound so that the target composition is achieved. In addition, a powder composition may be prepared by mixing necessary amounts of an iron compound, a cobalt compound, and an aluminum compound into a zirconia powder that is stabilized with at least either yttria or erbia. Furthermore, a powder composition may be formed by producing multiple types of colored zirconia mixed powders containing each colorant and mixing the colored zirconia mixed powders so as to achieve the desired composition.

A more specific example of a powder composition is a powder composition obtained by the following method.

A mixed powder prepared by mixing 0.05 wt. % of alumina into a zirconia powder that is stabilized with 5.5 mol % of yttria (called "powder 1" hereafter) and a mixed powder prepared by mixing 0.05 wt. % of alumina into a zirconia powder that is stabilized with 3.2 mol % of erbia (called "powder 2" hereafter) are respectively produced. Furthermore, a mixed powder prepared by mixing 2,500 ppm of an iron compound in terms of $Fe_2O_3$ and 0.05 wt. % of alumina into a zirconia powder that is stabilized with 5.5 mol % of yttria (called "powder 3" hereafter) and a mixed powder prepared by mixing 0.04 wt. % of a cobalt compound in terms of CoO and 0.05 wt. % of alumina into a similar zirconia powder (called "powder 4" hereafter) are respectively produced.

A powder composition is prepared by uniformly mixing powders 1 to 4 so that the $Er_2O_3$, $Fe_2O_3$, and CoO contents are the target contents. By adjusting the mixing ratios of powders 1 to 4, it is possible to prepare a powder composition with which a sintered body having a color tone of the VITA shade can be obtained.

The BET specific surface area of the powder composition is preferably from 7 to 13 $m^2/g$, more preferably from 8 to 12 $m^2/g$, and even more preferably from 10 to 12 $m^2/g$. When the BET specific surface area is not less than 7 $m^2/g$, the powder becomes easy to pulverize. In addition, when the BET specific surface area is not greater than 13 $m^2/g$, the density of the resulting sintered body is unlikely to become low.

The powder composition preferably is composed of spray-granulated powder granules (also simply called "granules" hereafter), and preferably is composed of granules containing an organic binder. By granulating the zirconia powder composition, the flowability of the powder becomes high when forming a green body, and pores are easily removed from the green body. As a result, air bubbles are unlikely to generate in the sintered body.

Examples of organic binders include ordinarily used organic binders such as polyvinyl alcohol, polyvinyl butyrate, waxes, and acrylic binders. Of these, acrylic binders having carboxyl groups or derivatives thereof (for example, salts; in particular, ammonium salts or the like) in the molecule are preferable. Examples of acrylic organic binders include polyacrylic acids, polymethacrylic acids, acrylic acid copolymers, methacrylic copolymers, and derivatives thereof. The added amount of the organic binder is preferably from 0.5 to 10 wt. % and more preferably from 1 to 5 wt. % with respect to the zirconia powder composition in the zirconia powder slurry.

A particularly preferable powder composition used in the molding step (also called the "powder composition of the present invention" hereafter) is a powder composition comprising powders having approximately the same thermal shrinkage rate. When the powder composition of the present invention comprises powders having approximately the same thermal shrinkage rate, it is possible to finely control the aesthetics of the obtained sintered body by simply adjusting the proportion of each powder in the powder composition. As a result, it is possible to more easily produce a sintered body having the aesthetics of a natural front tooth and having a series of color tones of a shade guide.

An example of a powder composition which comprises powders having approximately the same thermal shrinkage rates and with which a sintered body having the aesthetics of a natural front tooth can be obtained is a zirconia powder composition containing at least two types selected from the group consisting of: a zirconia mixed powder containing greater than 0 wt. % and less than 0.09 wt. % of alumina, the remainder being zirconia stabilized with greater than 4 mol % and not greater than 6.5 mol % of yttria (also called an "Al—Y-containing $ZrO_2$ powder" hereafter); a zirconia mixed powder containing greater than 0 wt. % and less than 0.09 wt. % of alumina and not less than 2,000 ppm and not greater than 3,000 ppm of an iron compound in terms of $Fe_2O_3$, the remainder being zirconia stabilized with greater than 4 mol % and not greater than 6.5 mol % of yttria (also called an "Fe—Al—Y-containing $ZrO_2$ powder" hereafter); a zirconia mixed powder containing greater than 0 wt. % and less than 0.09 wt. % of alumina and not less than 0.03 wt. % and not greater than 0.05 wt. % of a cobalt compound in terms of CoO, the remainder being zirconia stabilized with greater than 4 mol % and not greater than 6.5 mol % of yttria (also called a "Co—Al—Y-containing $ZrO_2$ powder" hereafter); and a zirconia mixed powder containing greater than 0 wt. % and less than 0.09 wt. % of alumina, the remainder being zirconia stabilized with greater than 2 mol % and not greater than 5 mol % of erbia (also called an "Al—Er-containing $ZrO_2$ powder" hereafter).

In the powder composition of the present invention, the alumina content of each of the Al—Y-containing $ZrO_2$ powder, the Fe—Al—Y-containing $ZrO_2$ powder, and the Co—Al—Y-containing $ZrO_2$ powder is preferably not less than 0.045 wt. % and not greater than 0.055 wt. %. In addition, the zirconia in each of the Al—Y-containing $ZrO_2$ powder, the Fe—Al—Y-containing $ZrO_2$ powder, and the Co—Al—Y-containing $ZrO_2$ powder is preferably stabilized with not less than 4.6 mol % and not greater than 6 mol %, more preferably not less than 5 mol % and less than 6 mol %, and even more preferably not less than 5.1 mol % and not greater than 5.5 mol % of yttria. Furthermore, the zirconia in the Al—Er-containing $ZrO_2$ powder is preferably stabilized with greater than 2 mol % and not greater than 4.5 mol %, more preferably not less than 2.5 mol % and not greater than 4 mol %, and even more preferably not less than 2.5 mol % and not greater than 3.5 mol % of erbia.

The content of the iron compound in the Fe—Al—Y-containing $ZrO_2$ powder is preferably not less than 2,200 ppm and not greater than 2,800 ppm and more preferably not less than 2,300 ppm and not greater than 2,600 ppm in terms of $Fe_2O_3$.

In the powder composition of the present invention, the BET specific surface area of the Al—Er-containing $ZrO_2$ powder may be larger than the BET specific surface areas of the Al—Y-containing $ZrO_2$ powder, the Fe—Al—Y-containing $ZrO_2$ powder, and the Co—Al—Y-containing $ZrO_2$ powder. The BET specific surface area of the Al—Er-containing $ZrO_2$ powder may be not less than 1.5 $m^2/g$ greater than the specific surface areas of the Al—Y-containing $ZrO_2$ powder, the Fe—Al—Y-containing $ZrO_2$ powder, and the Co—Al—Y-containing $ZrO_2$ powder. Furthermore, in the powder composition of the present invention, the BET specific surface areas of the Al—Y-containing $ZrO_2$ powder, the Fe—Al—Y-containing $ZrO_2$ powder, and the Co—Al—Y-containing $ZrO_2$ powder are preferably not less than 7 $m^2/g$ and less than 13 $m^2/g$, more preferably not less than 8 $m^2/g$ and not greater than 11.5 $m^2/g$, and even more preferably not less than 8 $m^2/g$ and not greater than 10.5 $m^2/g$. In addition, the BET specific surface area of the Al—Er-containing $ZrO_2$ powder is preferably larger than that of the other powders in the powder composition, and is preferably not less than 9 $m^2/g$ and not greater than 14 $m^2/g$ and more preferably not less than 10 $m^2/g$ and not greater than 14 $m^2/g$.

Furthermore, in the powder composition of the present invention, at least one powder selected from the group consisting of the Al—Y-containing $ZrO_2$ powder, the Fe—Al—Y-containing $ZrO_2$ powder, the Co—Al—Y-containing $ZrO_2$ powder, and the Al—Er-containing $ZrO_2$ powder preferably comprises granules, and the average granule size of the powder composition is preferably less than 48 μm, more preferably not less than 30 μm and less than 48 μm, and even more preferably not less than 40 μm and not greater than 45 μm.

The theoretical density of a sintered body obtained by the production method of the present invention, in particular, a sintered body obtained using the powder composition of the present invention, may be obtained using the following equation from the ratio of each of the Al—Y-containing $ZrO_2$ powder, the Fe—Al—Y-containing $ZrO_2$ powder, the Co—Al—Y-containing $ZrO_2$ powder, and the Al—Er-containing $ZrO_2$ powder in the powder composition and the theoretical density of a sintered body that would hypothetically be obtained from each of these mixed powders.

$$\rho_0 = 100/[(w/\rho w) + (y/\rho y) + (g/\rho g) + (100-w-y-g)/\rho p] \quad (3)$$

In Equation (3), $\rho_0$ is theoretical density (g/cm³) of the sintered body of the present invention; w is the weight ratio (wt. %) of the Al—Y-containing $ZrO_2$ powder in the powder composition of the present invention; y is the weight ratio (wt. %) of the Fe—Al—Y-containing $ZrO_2$ powder in the powder composition of the present invention; g is the weight ratio (wt. %) of the Co—Al—Y-containing $ZrO_2$ powder in the powder composition of the present invention; ρw is the theoretical density (g/cm³) of a sintered body obtained from an Al—Y-containing $ZrO_2$ powder; ρy is the theoretical density (g/cm³) of a sintered body obtained from an Fe—Al—Y-containing $ZrO_2$ powder; ρg is the theoretical density (g/cm³) of a sintered body obtained from a Co—Al—Y-containing $ZrO_2$ powder; and ρp is the theoretical density (g/cm³) of a sintered body obtained from an Al—Er-containing $ZrO_2$ powder.

In Equation (3), the theoretical density of a sintered body obtained from an Al—Er-containing $ZrO_2$ powder may be the density of a sintered body obtained by sintering the mixed powder for 2 hours or longer at 1,350 to 1,500° C. and then performing HIP treatment for 1 hour or longer at 1,300 to 1,450° C. at 150 MPa. In addition, the theoretical densities of sintered bodys obtained from the other mixed powders can be easily determined from Equation (1).

For example, when a sintered body is produced from a zirconia mixed powder containing 0.05 wt. % of alumina, the remainder being 5.5 mol % of yttria-containing zirconia, as an Al—Y-containing $ZrO_2$ powder, the theoretical density of the sintered body can be determined to be 6.0508 g/cm³ from Equation (1).

Similarly, when a sintered body is produced from a mixed powder containing 0.05 wt. % of alumina and 2,500 ppm of an iron compound, the remainder being 5.5 mol % of yttria-containing zirconia, as an Fe—Al—Y-containing $ZrO_2$ powder, the theoretical density of the sintered body can be determined to be 6.0485 g/cm³ from Equation (1).

Similarly, when a sintered body is produced from a mixed powder containing 0.05 wt. % of alumina and 0.04 wt. % of a cobalt compound, the remainder being 5.5 mol % of yttria-containing zirconia, as a Co—Al—Y-containing $ZrO_2$ powder, the theoretical density of the sintered body can be determined to be 6.0509 g/cm³.

In addition, when a sintered body is produced from a zirconia mixed powder containing 0.05 wt. % of alumina, the remainder being zirconia stabilized with 3.2 mol % of erbia, as an Al—Er-containing $ZrO_2$ powder, the density of a sintered body obtained by the primary firing and HIP treatment described above (6.336 g/cm³) may be used.

With the production method of the present invention, a powder composition can be molded. Any molding method may be used, but an example is at least one type of molding method selected from the group consisting of press molding, cold isostatic pressing, slip casting, sheet molding, and injection molding.

In the sintering step, the green body obtained in the molding step is sintered under normal pressure at a sintering temperature of from 1,400 to 1,600° C. As a result, the sintered body of the present invention is obtained.

The sintering temperature in the sintering step is preferably not lower than 1,400° C. and not higher than 1,490° C., more preferably not lower than 1,410° C. and not higher than 1,480° C., and even more preferably not lower than 1,410° C. and not higher than 1,470° C.

The heating rate in the sintering step is not greater than 800° C./hour and preferably not greater than 600° C./hour. A preferable heating rate is not less than 150° C./hour and not greater than 800° C./hour or not less than 400° C./hour and not greater than 700° C./hour. As a result, it is possible to suppress the progression of sintering in the heating process and to sinter the green body at the sintering temperature.

The retention time at the sintering temperature (also simply called the "retention time" hereafter) differs depending on the sintering temperature. The retention time may be not greater than 5 hours, not greater than 3 hours, or not greater than 2 hours.

The sintered body of the present invention is sintered under normal pressure. Sintering under normal pressure is a method of sintering by simply heating without applying any external force to the green body (also called "pressureless sintering" hereafter). A specific example of pressureless sintering is sintering under atmospheric pressure.

The sintering atmosphere should be an atmosphere other than a reducing atmosphere. The sintering atmosphere should not be a reducing atmosphere, and an atmospheric environment of at least either an oxygen atmosphere or an atmospheric environment is preferable and an atmospheric environment is easy to achieve.

A particularly preferable sintering step entails sintering under atmospheric pressure, a heating rate of not less than 350° C./hour and not greater than 650° C./hour, and a sintering temperature of not lower than 1,400° C. and not higher than 1,490° C.

The sintering step preferably includes only sintering under normal pressure. A typical means for enhancing translucency is to use a special sintering method such as HIP or another pressure sintering method or SPS after pressureless sintering. However, special sintering methods not only complicate the production process, but also cause an increase in production cost. When the production method of the present invention, in particular, the powder composition of the present invention, is used, a colored translucent zirconia sintered body having both sufficient aesthetics and strength as a front tooth denture can be obtained by sintering under normal pressure alone.

EXAMPLES

The present invention will be described in detail with reference to examples hereinafter. However, the present invention is not limited to these examples.

Average Particle Size of Powder

The average particle size of a zirconia powder was measured using a Microtrac particle size distribution analyzer (device name: 9320-HRA, manufactured by Honeywell Co., Ltd.).

As pretreatment, a sample powder was suspended in distilled water to form a slurry, and this was subjected to dispersion treatment for 3 minutes using an ultrasonic homogenizer (device name: US-150T, manufactured by the NISSEI Corporation).

Crystal Phase of Powder

The crystal phase of the powder sample was measured by XRD measurement. The tetragonal and cubic phase ratio (also called the "T+C phase ratio" hereafter) in a powder sample was determined from the obtained XRD pattern. The T+C phase ratio was calculated from the following equation.

$T+C$ phase ratio (%)=100−$fm$ (%)

In the above equation, fm is the monoclinic phase ratio.

Average Granule Size of Granules

The average granule size of a granulated sample was determined by a sieve test method.

Average Crystal Grain Size of Sintered Body

The average crystal grain size of a sintered body sample was determined by a planimetric method from an SEM photograph obtained by field emission scanning electron microscopy (FESEM). That is, a mirror-polished sintered body sample was subjected to thermal etching, and this was observed using a field emission scanning electron microscope (device name: JSM-T220, manufactured by JEOL Ltd.). The average crystal grain size was calculated by a planimetric method from the obtained SEM photograph.

Sintered Body Density

The measured density of a sintered body was measured by Archimedes' method.

Total Light Transmittance

The total light transmittance of a sintered body was measured using a spectrophotometer (device name: V-650, manufactured by the JASCO Corporation). Using disc-shaped sintered body polished on both sides with a thickness of 1 mm as a measurement sample, light with a wavelength of from 220 to 850 nm was transmitted through the sample, and the light concentrated with an integrating sphere was measured.

D65 Transmittance

The total light transmittance with a D65 light source was measured by a method according to JIS K 7361 using a turbidity meter (device name: NDH2000, manufactured by Nippon Denshoku Industries Co., Ltd.).

The same sample as that used in the measurement of the 600 nm transmittance was used as a measurement sample.

Color Tone

The color tone of a sintered body was measured by a method according to JIS Z8729. A color difference meter (device name: Z-300, manufactured by Nippon Denshoku Industries Co., Ltd.) was used for measurements.

A disc-shaped sintered body polished on one side with a thickness of 2.8 mm was used for measurements. Color tone measurements were performed for the polished side of the sintered body.

Color Tone Difference

The color tones of a sintered body sample before and after being immersed for 24 or 72 hours in hot water at 140° C. was measured. The color tone difference (ΔE) was determined by the following equation using the resulting color tones.

$$\Delta E = (\Delta L^{*2} + \Delta a^{*2} + \Delta b^{*2})^{1/2}$$

Strength

The three-point bending strength was measured as the strength of a sintered body sample. Measurements were performed using a three-point bending measurement method based on the method described in JIS R 1601.

Working Examples 1 to 16

Synthesis of Alumina/Yttria-Containing Zirconia Granulated Powder

A hydrated zirconia sol was obtained by performing a hydrolysis reaction on a zirconium oxychloride aqueous solution. After yttrium chloride was added to the hydrated zirconia sol so that the yttria concentration was 5.5 mol %, the sample was dried and calcined for 2 hours at 1,160° C. to obtain a zirconia calcined powder containing 5.5 mol % of yttria.

The obtained calcined powder was washed with distilled water, and α-alumina having an average particle size of 0.3 μm was added to the zirconia powder so that the alumina content was 0.05 wt. %.

A slurry was formed by adding distilled water to the mixed powders so that the solid content concentration of these mixed powders was 45 wt. %. Using zirconia balls with a diameter of 2 mm, the slurry was pulverized for 20 hours with a ball mill so that the average particle size was from 0.40 to 0.50 μm, and a zirconia mixed powder containing 0.05 wt. % of alumina, the remainder being zirconia stabilized with 5.5 mol % of yttria, was obtained (also called a "Y-type mixed powder" hereafter). The evaluation results for the powder are shown in Table 1.

Next, 3 wt. % of an organic binder was added to the obtained slurry after pulverization, and the sample was then spray-dried to granulate the mixed powder. The obtained granules had an average granule size of 44 μm and an light duty bulk density of 1.24 g/cm$^3$.

Synthesis of Alumina/Yttria/Iron Oxide-Containing Zirconia Granulated Powder

A zirconia calcined powder containing 5.5 mol % of yttria was obtained by calcination under the same conditions as those described above. After the calcined powder was washed with distilled water and dried, 0.05 wt. % of alumina content was added and 2,500 ppm by weight of iron oxide hydroxide (FeOOH) was added to the zirconia powder in terms of $Fe_2O_3$ to form a mixed powder. A slurry was formed by adding distilled water to the mixed powders so that the solid content concentration of these mixed powders was 45 wt. %. Using zirconia balls with a diameter of 2 mm, the obtained slurry was pulverized for 20 hours with a ball mill so that the average particle size was from 0.40 to 0.50 μm to obtain a zirconia mixed powder containing 0.05 wt. % of alumina and 2,500 ppm by weight of iron oxide hydroxide, the remainder being zirconia stabilized with 5.5 mol % of yttria (also called an "Fe-containing Y-type mixed powder" hereafter). The evaluation results for the powder are shown in Table 1.

Next, 3 wt. % of an organic binder was added to the obtained slurry after pulverization, and the sample was then spray-dried to granulate the Fe-containing Y-type mixed powder. The obtained granules had an average granule size of 44 μm and an untamped density of 1.24 g/cm$^3$.

Synthesis of Alumina/Yttria/Cobalt Oxide-Containing Zirconia Granulated Powder

A zirconia calcined powder containing 5.5 mol % of yttria was obtained by calcination under the same conditions as those described above. After the calcined powder was washed with distilled water and dried, 0.05 wt. % of alumina content was added and 0.04 wt. % of cobalt oxide was added to the zirconia powder in terms of CoO to form a mixed powder. A slurry was formed by adding distilled water to the mixed powders so that the solid content concentration of these mixed powders was 45 wt. %. Using zirconia balls with a diameter of 2 mm, the obtained slurry was pulverized for 20 hours with a ball mill so that the average particle size was from 0.40 to 0.50 μm, and a zirconia mixed powder containing 0.05 wt. % of alumina and 0.04 wt. % of cobalt oxide, the remainder being zirconia stabilized with 5.5 mol % of yttria, was obtained (also called a "Co-containing Y-type mixed powder" hereafter). The evaluation results for the powder are shown in Table 1.

The average particle size of the Co-containing Y-type mixed powder in the obtained slurry was 0.42 μm, and the maximum particle size was ≤1.5 μm. The BET specific surface area of the dried Co-containing Y-type mixed powder was 10.1 m$^2$/g, and the crystallite size was 390 Å. The M-phase ratio of the dried powder was ≤1%.

Next, 3 wt. % of an organic binder was added to the obtained slurry after pulverization, and the sample was then spray-dried to granulate the mixed powder. The obtained granules had an average granule size of 45 μm and an light duty bulk density of 1.25 g/cm$^3$.

Synthesis of Alumina/Erbia-Containing Zirconia Granulated Powder

First, $Er_2O_3$ was added to a hydrated zirconia sol obtained by performing a hydrolysis reaction on a zirconium oxychloride aqueous solution so that the $Er_2O_3$ concentration was 3.2 mol %, and after the sample was dried, the sample was calcined for 2 hours at a calcination temperature of 1,100° C. to obtain a calcined powder.

After the obtained calcined powder was washed with water and dried, α-alumina was added to the zirconia powder so that the alumina content was 0.05 wt. % to form a mixed powder.

A slurry was formed by adding distilled water so that the solid content concentration of these mixed powders was 45 wt. %. Using zirconia balls with a diameter of 2 mm, the obtained slurry was pulverized for 26 hours with a ball mill so that the average particle size was from 0.40 to 0.50 μm to obtain a zirconia mixed powder containing 0.05 wt. % of alumina, the remainder being zirconia stabilized with 3.2 mol % of erbia (also called an "Er-type mixed powder" hereafter). The evaluation results for the powder are shown in Table 1.

The average particle size of the Er-type mixed powder in the obtained slurry after pulverization was 0.42 μm, and the maximum particle size was ≤1.5 μm. The BET specific surface area of the dried Er-type mixed powder was 12.0 m$^2$/g, and the crystallite size was 340 Å. The M-phase ratio of the dried powder was 39%.

TABLE 1

| | Average particle size (μm) | Maximum particle size (μm) | BET specific surface area (m$^2$/g) | Crystallite size (Å) | M-phase ratio (%) |
|---|---|---|---|---|---|
| Y-type mixed powder | 0.43 | 1.5 | 10.2 | 390 | ≤1 |
| Fe-containing Y-type mixed powder | 0.42 | 1.5 | 10.1 | 390 | ≤1 |
| Co-containing Y-type mixed powder | 0.42 | 1.5 | 10.1 | 390 | ≤1 |
| Er-type mixed powder | 0.42 | 1.5 | 12.0 | 340 | 39 |

Sintered Body Production

Two or more types of the Y-type mixed powder, the Fe-containing Y-type mixed powder, the Co-containing Y-type mixed powder, and the Er-type mixed powder were mixed in a polyethylene bottle in order to achieve each of the compositions of Working Examples 1 to 16 in Table 2, and powder compositions were thereby obtained.

After the obtained powder compositions were preliminarily molded by uniaxial pressing at 19.6 MPa, the premolded products were molded by cold isostatic pressing (CIP) at 196 MPa to obtain green bodies. The obtained green bodies were sintered by pressureless sintering under conditions with a sintering temperature of 1,450° C., a heating rate of 600° C./hour, and a retention time of 2 hours to obtain the colored translucent zirconia sintered bodies of Working Examples 1 to 16. The evaluation results of the obtained colored translucent zirconia sintered bodies are shown in Table 2.

Note that in these working examples, the theoretical density (ρ') of each sintered body was determined as follows by determining the theoretical density of a sintered body that would hypothetically be obtained from each mixed powder.

The theoretical density of a zirconia sintered body containing 0.05 wt. % of alumina and 5.5 mol % of yttria was determined from Equation (1) to be 6.0508 g/cm$^3$.

The theoretical density of a zirconia sintered body containing 0.05 wt. % of alumina, 5.5 mol % of yttria, and 2,500 ppm of iron oxide was determined from Equation (1) to be $100/[(0.05/3.99)+(0.25/5.24)+(99.80/6.0508)]=6.0485$ g/cm$^3$ (called "ρy'" hereafter).

The theoretical density of a zirconia sintered body containing 0.05 wt. % of alumina, 5.5 mol % of yttria, and 0.04 wt. % of cobalt oxide was determined from Equation (1) to be $100/[(0.05/3.99)+(0.04/5.24)+(99.91/6.0508)]=6.0509$ g/cm$^3$ (called "ρg'" hereafter).

The theoretical density of a zirconia sintered body containing 0.05 wt. % of alumina and 3.2 mol % of erbia was determined to be the HIP sintered body density of 6.336 g/cm$^3$ (called "ρp'" hereafter).

The theoretical density $\rho_0'$ was determined by Equation (3)' from the theoretical density of the sintered body of each composition described above and the compounding ratios (weight ratios) thereof.

$$\rho_0'=100/[(w'/\rho w')+(y'/\rho y')+(g'/\rho g')+(100-w'-y'-g')/\rho p'] \quad (3)'$$

In Equation (3)', w' is the compounding ratio (wt. %) of zirconia containing 0.05 wt. % of alumina and 5.5 mol % of yttria; y' is the compounding ratio (wt. %) of zirconia containing 0.05 wt. % of alumina, 2,500 ppm of iron oxide, and 5.5 mol % of yttria; and g' is the compounding ratio (wt. %) of zirconia containing 0.05 wt. % of alumina, 0.04 wt. % of cobalt oxide, and 5.5 mol % of yttria.

The colorant content in the table below is the total content (wt. %) of erbium oxide, cobalt oxide, and iron oxide, and "-" in the table indicates unmeasured data.

TABLE 2

| | $Y_2O_3$ (mol %) | $Er_2O_3$ (mol %) | $Fe_2O_3$ (ppm) | CoO (wt. %) | $Al_2O_3$ (wt. %) | Total colorant content (wt. %) | Measured density (g/cm$^3$) | Relative density (%) |
|---|---|---|---|---|---|---|---|---|
| Working Example 1 | 5.38 | 0.07 | 600 | 0 | 0.05 | 0.80 | 6.052 | 99.93 |
| Working Example 2 | 5.23 | 0.15 | 850 | 0 | 0.05 | 1.29 | 6.057 | 99.90 |
| Working Example 3 | 5.26 | 0.14 | 900 | 0 | 0.05 | 1.31 | 6.056 | 99.91 |
| Working Example 4 | 5.17 | 0.19 | 1300 | 0 | 0.05 | 1.85 | 6.061 | 99.92 |
| Working Example 5 | 5.15 | 0.21 | 1400 | 0.0025 | 0.05 | 2.04 | 6.063 | 99.90 |
| Working Example 6 | 5.41 | 0.05 | 600 | 0 | 0.05 | 0.75 | 6.052 | 99.96 |
| Working Example 7 | 5.38 | 0.07 | 800 | 0 | 0.05 | 1.00 | 6.053 | 99.95 |
| Working Example 8 | 5.32 | 0.10 | 900 | 0.0005 | 0.05 | 1.20 | 6.057 | 99.97 |
| Working Example 9 | 5.26 | 0.14 | 1100 | 0 | 0.05 | 1.51 | 6.056 | 99.91 |
| Working Example 10 | 5.44 | 0.03 | 500 | 0.0020 | 0.05 | 0.59 | 6.051 | 99.96 |
| Working Example 11 | 5.38 | 0.07 | 700 | 0.0025 | 0.05 | 0.93 | 6.052 | 99.93 |
| Working Example 12 | 5.50 | 0.00 | 1000 | 0.0040 | 0.05 | 1.00 | 6.045 | 99.92 |
| Working Example 13 | 5.44 | 0.03 | 1400 | 0.0055 | 0.05 | 1.54 | 6.048 | 99.91 |
| Working Example 14 | 5.32 | 0.10 | 800 | 0.0020 | 0.05 | 1.09 | 6.056 | 99.95 |
| Working Example 15 | 5.26 | 0.14 | 1100 | 0.0005 | 0.05 | 1.51 | 6.056 | 99.91 |
| Working Example 16 | 5.44 | 0.03 | 900 | 0.0025 | 0.05 | 1.01 | 6.047 | 99.90 |

| | D65 transmittance (%) | Total light transmittance (%) | L* | a* | b* | Strength (MPa) | Remarks |
|---|---|---|---|---|---|---|---|
| Working Example 1 | 44.2 | 36.1 | 58.6 | -1.3 | 9.6 | — | A1 (VITA) |
| Working Example 2 | 41.5 | 35.5 | 56.7 | 0.74 | 13.2 | — | A2 (VITA) |
| Working Example 3 | 41.2 | 35.0 | 57.6 | 0.59 | 14.1 | — | A3 (VTA) |
| Working Example 4 | 37.7 | 33.8 | 54.5 | 2.3 | 18.4 | 674 | A3.5 (VITA) |
| Working Example 5 | 34.0 | 31.2 | 50.9 | 2.9 | 16.4 | — | A4 (VITA) |
| Working Example 6 | 44.3 | 35.8 | 58.4 | -2.0 | 9.7 | — | B1 (VITA) |

TABLE 2-continued

| | | | | | | | |
|---|---|---|---|---|---|---|---|
| Working Example 7 | 43.1 | 35.3 | 57.2 | −1.2 | 12.8 | — | B2 (VITA) |
| Working Example 8 | 40.7 | 34.7 | 56.5 | 0.17 | 13.8 | 673 | B3 (VITA) |
| Working Example 9 | 39.7 | 34.4 | 56.8 | 0.95 | 16.8 | — | B4 (VITA) |
| Working Example 10 | 41.8 | 33.9 | 54.8 | −0.84 | 5.1 | — | C1 (VITA) |
| Working Example 11 | 39.6 | 33.1 | 53.5 | 0.05 | 7.9 | — | C2 (VITA) |
| Working Example 12 | 36.7 | 31.2 | 51.2 | −0.79 | 11.1 | — | C3 (VITA) |
| Working Example 13 | 32.1 | 28.7 | 47.9 | 1.1 | 13.9 | — | C4 (VITA) |
| Working Example 14 | 38.8 | 33.0 | 46.9 | 0.46 | 7.3 | — | D2 (VITA) |
| Working Example 15 | 38.9 | 33.9 | 47.4 | 0.99 | 11.3 | — | D3 (VITA) |
| Working Example 16 | 39.0 | 32.8 | 45.8 | −0.66 | 8.5 | — | D4 (VITA) |

The colored translucent zirconia sintered bodies obtained in Working Examples 4, 8, 12, and 16 were immersed for 24 or 72 hours in hot water at 140° C. The results of measuring the M-phase ratio after immersion for 72 hours are shown in Table 3.

TABLE 3

| | M-phase ratio (%) |
|---|---|
| Working Example 4 | ≤1 |
| Working Example 8 | ≤1 |
| Working Example 12 | ≤1 |
| Working Example 16 | ≤1 |

As a result, it was confirmed that the sintered body of the present invention is resistant to changes in the crystal phase. In addition, the color tones of the sintered bodies after being immersed for 24 or 72 hours in hot water at 140° C. were measured. The results for the color tone of each sintered body and the color tone change (ΔE) relative to the sintered body before immersion are shown in Table 4.

TABLE 4

| | After immersion for 24 hours | | | | After immersion for 72 hours | | | |
|---|---|---|---|---|---|---|---|---|
| | L* | a* | b* | ΔE | L* | a* | b* | ΔE |
| Working Example 4 | 54.3 | 2.4 | 18.3 | 0.24 | 54.6 | 2.3 | 18.1 | 0.32 |
| Working Example 8 | 56.6 | 0.27 | 13.7 | 0.17 | 56.7 | 0.38 | 13.6 | 0.35 |
| Working Example 12 | 57.1 | 0.95 | 16.7 | 0.32 | 57.5 | 0.95 | 16.9 | 0.71 |
| Working Example 16 | 51.3 | −0.73 | 11.1 | 0.12 | 51.4 | −0.59 | 11.0 | 0.30 |

The color tone change ΔE of the sintered bodies after immersion for 24 hours was not greater than 0.32, and the color tone change ΔE after immersion for 72 hours was not greater than 0.71. As a result, even when the sintered body of the present invention is exposed to a water-containing environment, there was not only no change in the crystal phase, but there was also essentially no change in color tone. It was thereby confirmed that even when the sintered body of the present invention is used for a long period of time as a front tooth denture, there is no change in the aesthetics thereof.

Figure 1:
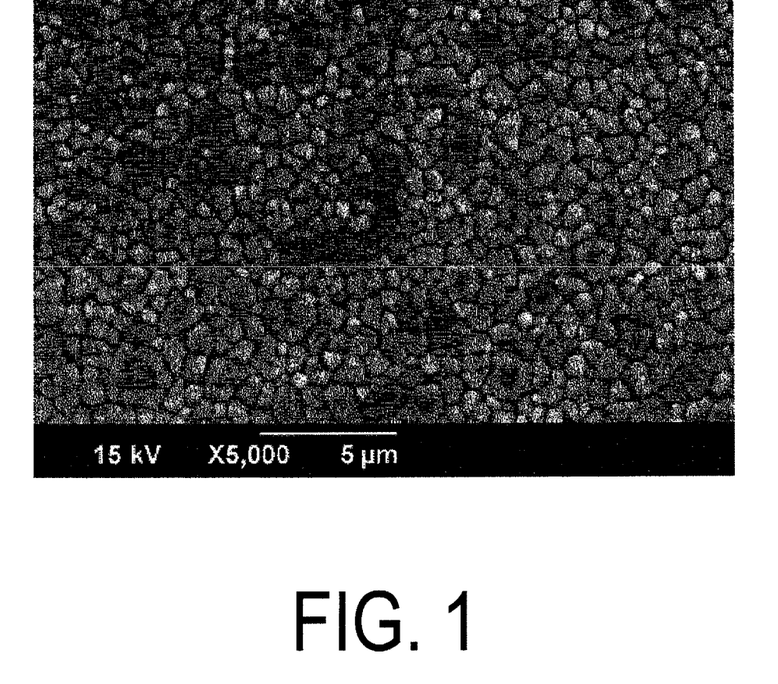
FIG. 1 is an SEM observation diagram of Working Example 4.

The microstructure of the colored translucent zirconia sintered body of Working Example 4 was observed by SEM. The results are illustrated in FIG. 1. The average crystal grain size of this sintered body was 0.80 μm, and the ratio of the number of small crystal grains to the number of large crystal grains was 1.6.

Figure 2:
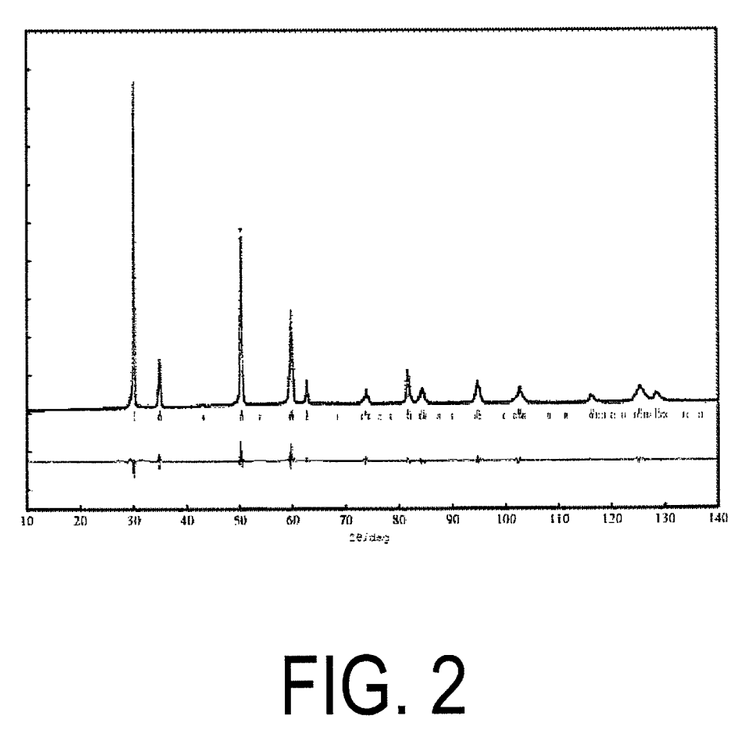
FIG. 2 is an XRD pattern of the colored translucent zirconia sintered body of Working Example 4.

An XRD pattern of the colored translucent zirconia sintered body of Working Example 4 was subjected to Rietveld analysis. The results are illustrated in FIG. 2. It was confirmed that the crystal phase of this sintered body comprises tetragonal and cubic phases, and it was determined that tetragonal crystals constitute 53% of the crystal phase, while cubic phases constitute 47% of the crystal phase.

INDUSTRIAL APPLICABILITY

The sintered body of the present invention is suitable as a dental material. The sintered body of the present invention is particularly suitable as a dental material for a front tooth and even more suitable as a denture, a mill blank, a disk, a bridge, an inlay, an onlay, a crown, or the like for a front tooth. Furthermore, the sintered body of the present invention can also be used in typical applications of zirconia sintered bodies such as other dental materials such as an orthodontic bracket, or materials other than dental materials such as jewelry, decorative materials, and structural materials.

All of the content of the specification, scope of patent claims, and abstract of Japanese Patent Application No. 2014-128263 filed on Jun. 23, 2014 is cited here and incorporated as a disclosure of the specification of the present invention.

The invention claimed is:

1. A colored translucent zirconia sintered body comprising zirconia containing greater than 4.0 mol % and not greater than 6.5 mol % of yttria, less than 0.25 mol % of erbia, less than 2,000 ppm of iron oxide in terms of $Fe_2O_3$, less than 0.01 wt. % of cobalt oxide in terms of CoO, and less than 0.1 wt. % of alumina; the zirconia sintered body having a relative density of not less than 99.90%, a total light transmittance of not less than 25% and less than 40% for light having a wavelength of 600 nm at a sample thickness of 1.0 mm, and a strength of not less than 500 MPa.

2. The colored translucent zirconia sintered body according to claim 1, wherein an average crystal grain size is from 0.3 to 5.0 μm.

3. The colored translucent zirconia sintered body according to claim 1, wherein a luminosity L* in an L*a*b color system is not less than 43 and not greater than 60.

4. The colored translucent zirconia sintered body according to claim 1, wherein a monoclinic phase transformation depth after being immersed for 24 hours in hot water at 140° C. is not greater than 5 μm.

5. The colored translucent zirconia sintered body according to claim 1, wherein a monoclinic phase ratio after being immersed for 72 hours in hot water at 140° C. is not greater than 5%.

6. The colored translucent zirconia sintered body according to claim 1, wherein a crystal phase contains tetragonal and cubic phases.

7. A production method for the colored translucent zirconia sintered body according to claim 1 comprising:
a molding step of obtaining a green body by molding a zirconia powder composition containing greater than 4.0 mol % and not greater than 6.5 mol % of yttria, less than 0.25 mol % of erbia, less than 0.1 wt. % of an aluminum compound in terms of $Al_2O_3$, less than 2,000 ppm of iron compound in terms of $Fe_2O_3$, and less than 0.01 wt. % of cobalt compound in terms of CoO; and
a sintering step of sintering the green body under normal pressure at 1,400 to 1,600° C.

8. The production method according to claim 7, wherein the zirconia powder composition contains at least two types selected from the group consisting of: a zirconia mixed powder containing greater than 0 wt. % and less than 0.09 wt .% of an aluminum compound, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 2,000 ppm and not greater than 3,000 ppm of an iron compound in terms of $Fe_2O_3$, the remainder being zirconia stabilized with greater than 4 mol % and not greater than 6.5 mol % of yttria; a zirconia mixed powder containing greater than 0 wt. % and less than 0.09 wt. % of an aluminum compound in terms of $Al_2O_3$ and not less than 0.03 wt. % and not greater than 0.05 wt. % of a cobalt compound in terms of CoO, the remainder being zirconia stabilized with greater than 4 mol % and not greater than 6.5 mol % of yttria; and a zirconia mixed powder containing greater than 0 wt. % and less than 0.09 wt. % of an aluminum compound in terms of $Al_2O_3$, the remainder being zirconia stabilized with greater than 2 mol % and not greater than 5 mol % of erbia.

9. The production method according to claim 7, wherein the iron compound is at least one selected from the group consisting of iron oxide hydroxide and iron oxide.

10. The production method according to claim 7, wherein the aluminum compound is alumina.

11. A dental material comprising the colored translucent zirconia sintered body according to claim 1.

* * * * *